US012651391B2

(12) United States Patent
    Zalev

(10) Patent No.:     US 12,651,391 B2
(45) Date of Patent:          Jun. 9, 2026

(54) SYSTEMS AND METHODS FOR OPTO-ACOUSTIC IMAGE RECONSTRUCTION WITH MULTIPLE ACQUISITIONS

(71) Applicant: OASignal Technologies, Inc., Thornhill (CA)

(72) Inventor: Jason Zalev, Thornhill (CA)

(73) Assignee: OASignal Technologies, Inc., Thornhill (CA)

( * ) Notice: Subject to any disclaimer, the term of this patent is extended or adjusted under 35 U.S.C. 154(b) by 732 days.

(21) Appl. No.: 17/665,571

(22) Filed: Feb. 6, 2022

(65) Prior Publication Data

US 2022/0262050 A1      Aug. 18, 2022

Related U.S. Application Data

(60) Provisional application No. 63/146,628, filed on Feb. 6, 2021.

(51) Int. Cl.
    *G06T 11/00*          (2026.01)
    *A61B 5/00*           (2006.01)
    (Continued)

(52) U.S. Cl.
    CPC .......... *G06T 11/006* (2013.01); *A61B 5/0095* (2013.01); *A61B 5/7207* (2013.01);
    (Continued)

(58) Field of Classification Search
    None
    See application file for complete search history.

(56) References Cited

U.S. PATENT DOCUMENTS

2011/0178739 A1*    7/2011  Tanji  ................... A61B 5/0059
                                                         702/56
2016/0296120 A1*   10/2016  Miyasa  ............... A61B 5/7207
                         (Continued)

FOREIGN PATENT DOCUMENTS

JP            2017018284  A  *  1/2017

OTHER PUBLICATIONS

Knauer et al., "Spatial Compounding of Volumetric Data Enables Freehand Optoacoustic Angiography of Large-Scale Vascular Networks", IEEE Transactions on Medical Imaging, vol. 39, No. 4., Apr. 2020, pp. 1160-1169. (Year: 2020).*
                         (Continued)

*Primary Examiner* — Katherine L Fernandez
(74) *Attorney, Agent, or Firm* — Jenna L. Wilson; Wilson Lue LLP (firm)

(57)          ABSTRACT

A method for opto-acoustic imaging with a probe includes delivering a first pulse of optical energy to an optically absorbing volume with the probe at a first configuration proximate to the volume; receiving acoustic responses of the first pulse from the probe; delivering a second pulse of optical energy to the volume with the probe at a second configuration proximate to the volume; receiving acoustic responses of the second pulse from the probe; computing a probe configuration estimate using the acoustic responses of the first and second pulses; computing an image of the volume using the computed estimate and the acoustic responses of the first and second pulses; and, displaying the image to a display.

8 Claims, 13 Drawing Sheets

(51) Int. Cl.
    *G06T 3/20*            (2006.01)
    *G06T 3/60*            (2006.01)

(52) U.S. Cl.
    CPC ................ *A61B 5/742* (2013.01); *G06T 3/20*
           (2013.01); *G06T 3/60* (2013.01); *G06T*
           *2210/41* (2013.01)

(56)           References Cited

U.S. PATENT DOCUMENTS

2017/0188993 A1\*   7/2017   Hamilton ............. A61B 8/0808
2018/0192881 A1\*   7/2018   Endo ................... A61B 5/0095

OTHER PUBLICATIONS

"Jacobian matrix and determinant", Wikipedia, Aug. 27, 2024, https://en.wikipedia.org/wiki/Jacobian_matrix_and_determinant (Year: 2024).\*
English translation of JP-2017-18284 (Year: 2017).\*

\* cited by examiner

ACQUISITION 1
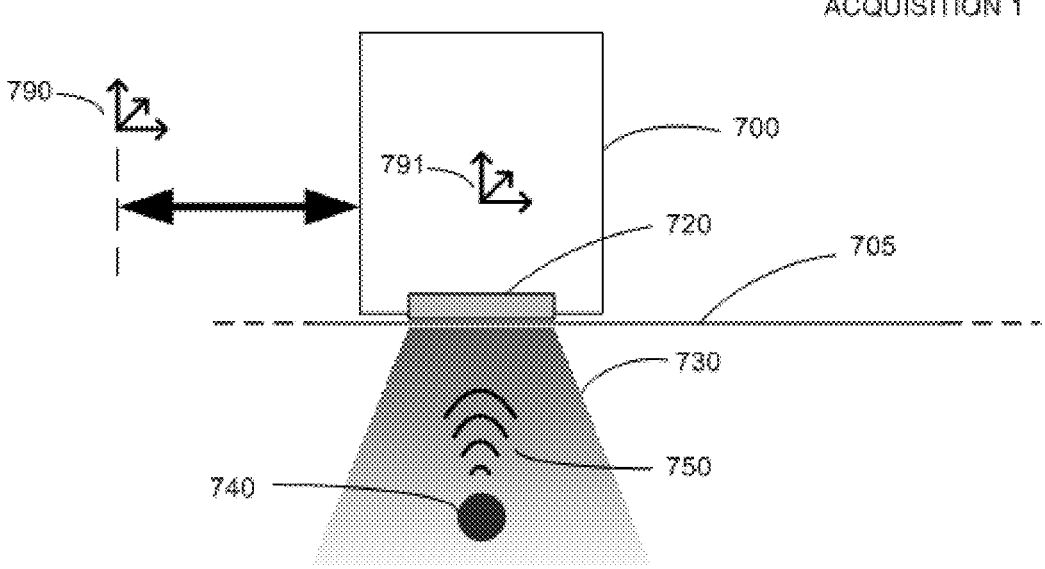
ACQUISITION 2
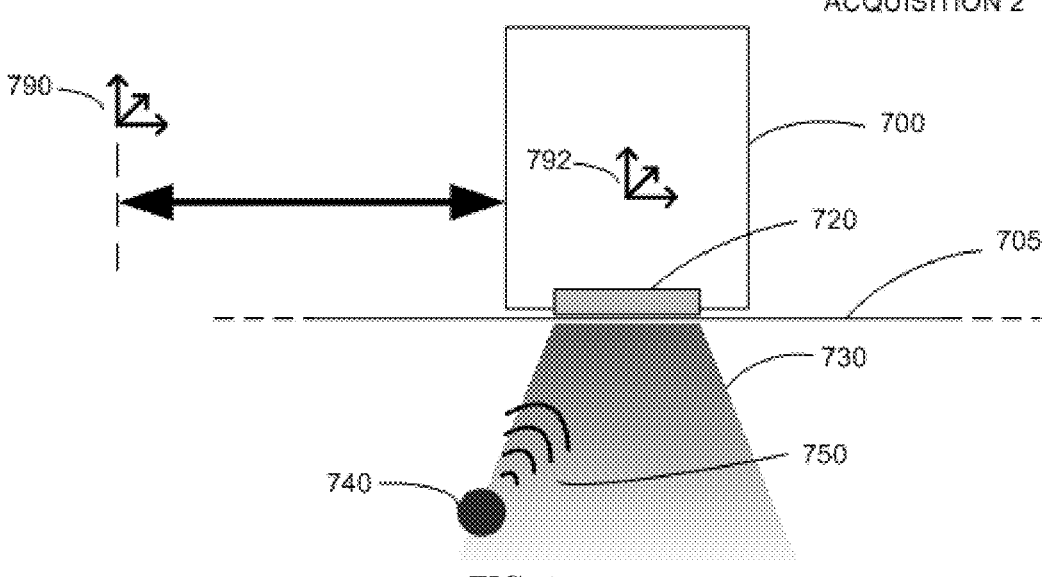
FIG. 1

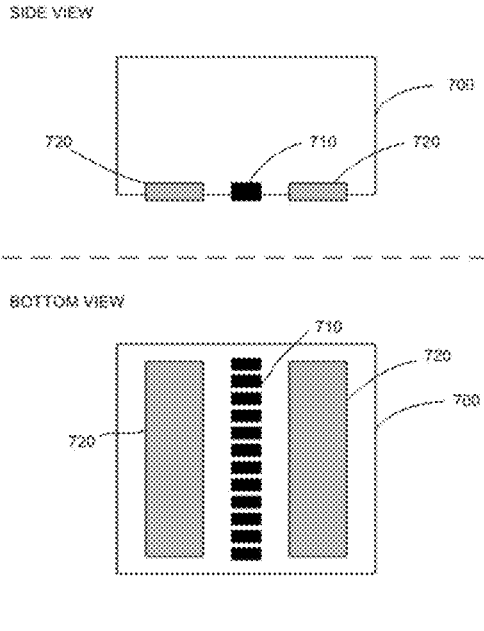
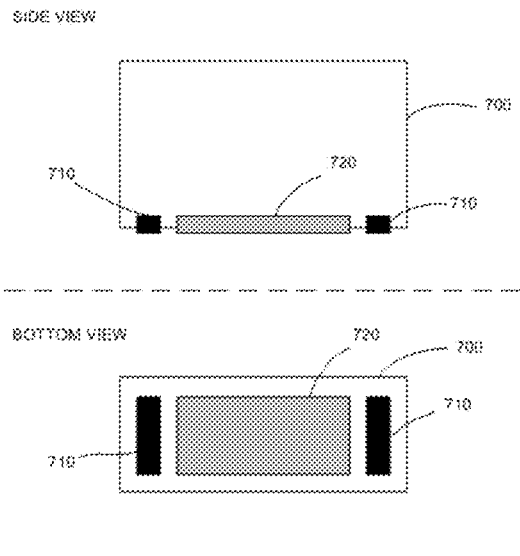
FIG. 6   A                              FIG. 6 B

SYSTEMS AND METHODS FOR OPTO-ACOUSTIC IMAGE RECONSTRUCTION WITH MULTIPLE ACQUISITIONS

TECHNICAL FIELD

The invention relates generally to the field of medical imaging, and more particularly to opto-acoustic imaging systems.

BACKGROUND

Opto-acoustic (OA) imaging systems detect acoustic waves produced by optical absorption to visualize molecular contrast in biological tissue. For proper tissue visualization, OA images with minimal clutter and distortion are desired. However, certain unwanted distortions and artifacts may arise during image reconstruction that are difficult to suppress. This occurs especially in 2D systems, where a hand-held probe incorporates an ultrasonic linear-array transducer with an integrated light delivery unit. To improve visibility, the present invention involves utilizing multiple acquisitions for 2D slices to perform reconstruction of 3D volumes.

SUMMARY OF THE INVENTION

Systems and methods are provided for opto-acoustic imaging wherein image reconstruction is combined with solving motion of a handheld probe using optimization algorithms. This can improve image quality when a probe does not follow a predetermined trajectory. Volumetric images are generated using acoustic responses received by the probe's transducers in response to delivered optical energy pulses. Positions and orientations of a probe's configuration, which are used during image reconstruction, are estimated using received acoustic responses. Images are computed by minimizing error between a measured response that is received by the probe's transducers and a predicted response that is generated by simulation from a reconstructed image based on a probe's rigid body configuration. To achieve real-time computational performance, a pipeline of results from earlier processing stages is stored in computer memory and used in subsequent computations. Rigid transformations are applied to stored results according to the probe's motion, which reduces computational requirements for subsequent reconstruction and motion solving processes. To further improve image quality, acquisition can be dynamically triggered by solving motion and computing time intervals to occur between successive optical pulses.

BRIEF DESCRIPTION OF THE DRAWINGS

For a more complete understanding of the invention, reference is made to the following description and accompanying drawings, in which:

FIG. 1 is illustrative of a probe with an initial configuration of position and orientation during a first acquisition (acquisition 1) and a different configuration during a second acquisition (acquisition 2).

FIG. 6 A) and FIG. 6 B) are illustrative of a probe 700 comprising at least one optical exit port 720 and at least one acoustic receiver 710.

DETAILED DESCRIPTION

Figure 2:
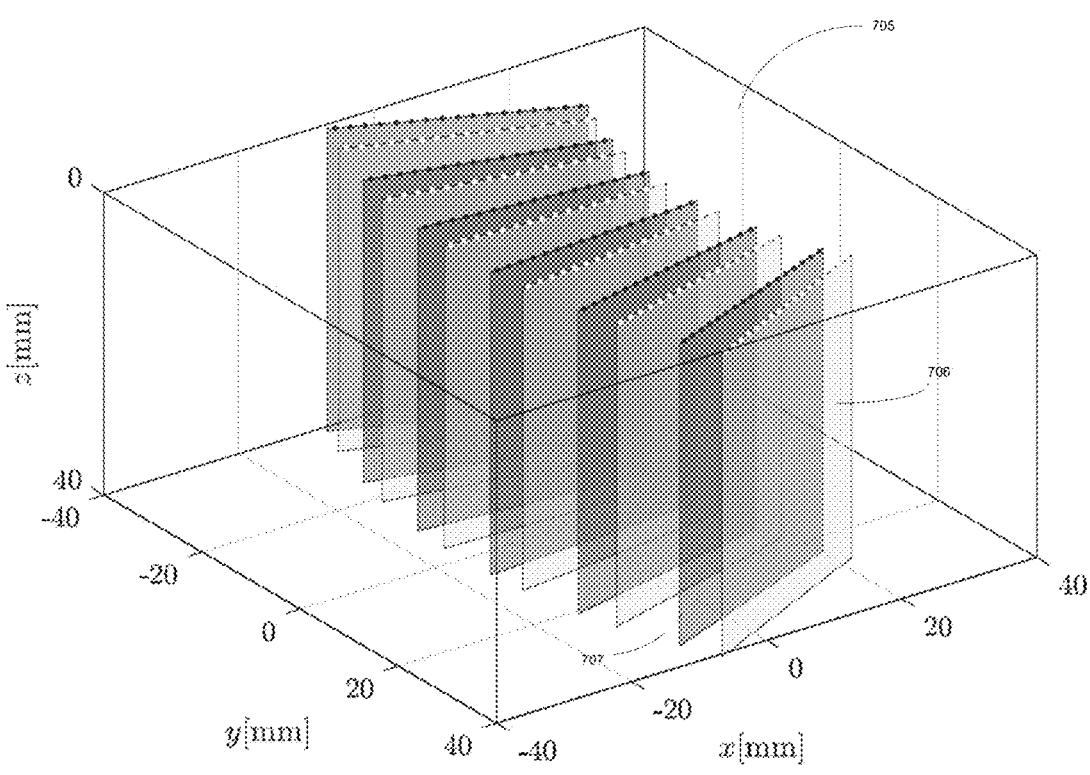
FIG. 2 is illustrative of a trajectory of frames that correspond with 2D slices in an optically absorbing volume.

Having summarized the invention above, certain exemplary and detailed embodiments will now be described below, with contrasts and benefits over the prior art being more explicitly described. The description and accompanying drawings are illustrative and are not to be construed as limiting. Numerous specific details are described to provide a thorough understanding. However, in certain instances, well-known or conventional details are not described in order to avoid obscuring the description.

References to one or an embodiment in the present disclosure are not necessarily references to the same embodiment; and, such references mean at least one. The phrase "in an embodiment" appearing in various places of this specification do not necessarily all refer to the same embodiment, nor are separate or alternative embodiments mutually exclusive of other embodiments. Reference to "an embodiment" or "the embodiment" means that a particular feature, structure, or characteristic described in connection with the embodiment is included in at least an embodiment of the disclosure. Various features or requirements are described which may be exhibited or required by some embodiments but not by others.

The present invention is described with reference to operational illustrations, block diagrams and algorithms pertaining to methods and devices for opto-acoustic imaging. It is understood that each block of the block diagrams, operational illustrations or algorithms, and combinations of blocks in the block diagrams, operational illustrations or algorithms, may be implemented by means of analog or digital hardware and computer program instructions. These computer program instructions may be stored on computer-readable media and provided to a processor of a general purpose computer, special purpose computer, ASIC, or other programmable data processing apparatus, such that the instructions, which execute via the processor of the computer or other programmable data processing apparatus, implements the functions/acts specified in the block diagrams or operational block or blocks. In some alternate implementations, the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

In some cases, block diagrams that illustrate processes with repeated steps (e.g. loops or iterations) do not indicate a criterion for exiting a sequence. This is not intended to imply that such a loop will never exit. It will be apparent to one skilled in the art that a suitable exit criterion can be used (e.g. termination after a fixed number of iterations, termination after a suitable fitness is achieved, etc.). In some cases, terms such as minimize, maximize, optimize or best-fit are used. This is intended to indicate that a strategy for finding a solution using such terms yields a good solution, but does not generally imply that an absolute global optimal solution must be achieved.

Certain embodiments of an opto-acoustic system are discussed in U.S. patent application Ser. No. 13/842,323 filed Mar. 15, 2013, entitled "Noise Suppression in an Optoacoustic System," the entirety of which is incorporated herein by this reference. In certain embodiments, opto-acoustic images can be displayed using parametric maps, which can be computed using the methods described in U.S. patent application Ser. No. 13/507,217, filed Jun. 13, 2012, entitled "System and Method for Acquiring Optoacoustic Data and Producing Parametric maps Thereof", the entirety of which is incorporated by reference herein. As well, certain embodiments of an opto-acoustic system are discussed in U.S. patent application Ser. No. 14/512,896 filed Oct. 13, 2014, entitled "Systems and Methods for Component Separation in Medical Imaging," which is incorporated herein by reference. Further embodiments are discussed in U.S. patent application Ser. No. 14/634,193 filed Feb. 27, 2015, entitled "Probe Having Light Delivery Through Combined Optically Diffusing and Acoustically Propagating Element," which is incorporated herein by this reference.

The present disclosure contains three main sections: A) Opto-acoustic Image Reconstruction with Solving Motion, B) Real-time Processing, and C) Uniform Motion Acquisition. In the Opto-acoustic Image Reconstruction with Solving Motion section, are disclosed novel methods and apparatus for processing opto-acoustic data, serving to enable the inclusion of estimated or known probe motions into image formation processes, and thereby improve the clarity of an opto-acoustic image based thereon. For example, this facilitates collecting volumetric information to improve 2D and 3D image reconstruction. Additional details relevant to this description, including additional results and outputs that may be obtained from applying the systems and methods described herein, may be found in "Opto-acoustic image reconstruction and motion tracking using convex optimization", by Jason Zalev et al., IEEE Trans. Computational Imaging, Vol 7, September 2021, at pp. 1161-1175, and Supplemental Materials thereof, the entirety of which is incorporated herein by reference.

The next main section of this disclosure, entitled Real-time Processing, expands on Opto-acoustic Image Reconstruction with Solving Motion to permit faster computation, and thereby can enable additional applications requiring more immediate display of generated outputs, as well as applications requiring continual operation of a processing pipeline.

The final section of this disclosure, entitled Uniform Motion Acquisition, expands on the earlier sections to dynamically and automatically perform triggering of acquisitions based on motion determined by techniques described herein, which can serve to improve image quality of resulting image output.

A) Opto-Acoustic Image Reconstruction with Solving Motion

Opto-acoustic imaging systems detect acoustic waves produced by optical absorption to visualize molecular contrast in biological tissue. This permits non-invasive vascular assessment of benign and malignant tumors. It will be apparent to one of skill in the art that hardware for opto-acoustic imaging systems typically includes an opto-acoustic probe that emits light and uses an ultrasonic transducer array to acquire opto-acoustic data, which can be used to visualize cross-sectional slices of tissue. OA reconstruction involves generating images to visualize molecular composition of tissue. To achieve this, acoustic transducer measurements are digitally processed to localize acoustic sources based on propagation delays. The use of multiple optical wavelengths allows molecular constituents to be determined from their optical absorption spectra.

For proper tissue visualization, reconstructed images should have minimal clutter and distortion. It will be apparent to one of skill in the art that although several analytic inversion formulas exist for performing OA reconstruction, these generally cause distortion unless a reconstructed region of tissue is fully surrounded by detectors to capture substantially all emitted acoustic waves. Consequently, the quality of analytic reconstruction approaches is limited by tissue surface acquisition because complete acoustic capturing is not generally applicable. To permit more accurate image reconstruction, convex optimization algorithms use assumptions about spatial smoothness and image sparsity to fit reconstructed images onto measured data, as is known by those of skill in the art. Such techniques can significantly improve contrast and reduce clutter. However, certain unwanted artifacts remain difficult to suppress, especially in 2D systems.

In 2D OA imaging, subjects are typically scanned using a hand-held probe that incorporates an ultrasonic linear-array transducer with an integrated light delivery unit. The light distribution, which depends on the illumination geometry and optical wavelength, cannot easily be confined to a 2D slice of tissue. This results in interfering acoustic waves produced by out-of-plane optical absorbers. Moreover, light intensity attenuates exponentially, which limits optical penetration and decreases image contrast in deep tissue. Obtaining additional surface measurements can potentially overcome these limitations by improving image contrast, interference suppression, and acoustic source localization. However, with free-hand acquired data, this requires the probe's position and orientation to be known and included in the reconstruction model. Consequently, there is a need for systems and methods that efficiently incorporate a probe's trajectory into OA reconstruction.

To improve visibility, in an embodiment of the present invention, multiple acquisitions corresponding to 2D slices are used to perform 3D volumetric reconstruction. In a preferred embodiment, this involves a computational model for a physical system that includes wavelength-specific optical absorption, position-dependent illumination and a realistic transducer element geometry. In an embodiment, motion of the probe is determined during an image reconstruction process, through a framework described herein, which involves computing an optimization algorithm. As described herein, this approach has potential to improve opto-acoustic image visibility for assessment of breast cancer or other diseases.

A method is described to reconstruct 3D images, which simultaneously solves motion of an OA probe. In an embodiment, volumetric reconstruction is performed from multiple 2D slices. This can facilitie interference suppression and improves image contrast in 2D and 3D. In an embodiment, the method uses sequential convex optimization to solve a non-linear optimization problem by solving a repeated convex problem. In an embodiment, measured acoustic data are fitted onto a model's predicted response. In an embodiment, a computational model comprises a wavelength-specific light distribution delivered from a probe's coordinate frame, and predicted acoustic responses, which are simulated based on 3D molecular composition of tissue. In an embodiment, fast computation is developed using a separable acoustic response matrix. Such fast computation is described in "Fast 3-D Opto-Acoustic Simulation for Linear Array with Rectangular Elements," by Zalev et al., IEEE Trans. Ultrasonics, Ferroelectrics, and Frequency Control, Vol. 68, No. 5, May 2021, at pp. 1885-1906, which is incorporated herein by reference.

Opto-Acoustic Signals

In opto-acoustic imaging, a probe delivers a rapid pulse of light, at optical wavelength $\lambda$, to the tissue surface. The radiant fluence $\varphi(\lambda, r)$ is the amount of light that reaches position r within the tissue. When light is absorbed, it is converted to an acoustic source distribution called the initial excess pressure $\psi(\lambda, r)$, which subsequently propagates as acoustic waves. This is equal to $$\psi(\lambda, r) = \eta(\lambda, r)\varphi(\lambda, r), \tag{1}$$

where $\eta(\lambda, r)$ is the opto-acoustic conversion efficiency, which is given by $$\eta(\lambda, r) = \gamma(r)\mu_a(\lambda, r). \tag{2}$$

Here, $\eta(\lambda, r)$ is the product of the tissue optical absorption coefficient $\mu_a(\lambda, r)$, which describes conversion of light to heat; and, the Grüneisen parameter $\gamma(r)$, which relates added heat to excess pressure. In tissue, $\gamma$ typically has a small spatial variation, and is often assumed to be constant. The parameter $\mu_a$ depends on the abundance of light-absorbing molecules called chromophores, which are spatially distributed based on the tissue composition, and can have widely different wavelength-specific optical properties from each other. In multi-wavelength imaging, this enables visualization of molecular tissue contrast. The tissue optical absorption $\mu_a$ is determined by a weighted linear combination $$\mu_a(\lambda, r) = \sum_i m_i(\lambda) \chi_i(r), \tag{3}$$

6 where $m_i(\lambda)$ is the optical absorption at wavelength $\lambda$, for the i-th chromophore, and $\chi_i(r)$ is its volume fraction abundance.

In an acoustically homogeneous medium, pressure waves due to $\psi(r, \lambda)$ propagate radially outward from r at a constant speed of sound $c_0$. The acoustic signal (a.k.a. acoustic response) measured by an acoustic transducer at position $r_0$, at time t, is $$y(\lambda, r_0, t) = \int_{\mathbb{R}^3} h(r_0 - r, t)\psi(\lambda, r)dr. \tag{4}$$

Here, the spatio-temporal impulse response for a transducer measurement is $$h(r, t) = \int_{-\infty}^{\infty} \int_{\mathbb{R}^3} g'(\tilde{r}, \tilde{t})f_a(r - \tilde{r})\alpha(\tilde{r})\beta(t - \tilde{t}) \, d\tilde{r} \, d\tilde{t}, \tag{5}$$

where $$g'(r, t) = \frac{\partial}{\partial t}\frac{\delta(\|r\| - c_0 t)}{4\pi t} \tag{6}$$

is the ideal impulse response for an infinitesimally-sized omni-directional transducer. In this equation, $\delta(t)$ is the Dirac delta function. In (5), the transducer aperture function $f_a(r)$ models the element geometry. For rectangular elements, this is $$f_a(r) = rect\left(\frac{r_1}{a_1}, \frac{r_2}{a_2}\right)\delta(r_3), \tag{7}$$

where $a_1$ and $a_2$ represent the element length and width, and the element is oriented normal to the $r_3$-axis, with coordinates $r=(r_1, r_2, r_3)$. The obliquity factor $$\alpha(r) = \frac{|r \cdot \hat{n}|}{\|r\|} \tag{8}$$

models the transducer directionality. Here, $\hat{n}$ is the outward normal to the transducer at r. For an omni-directional transducer, which does not include directionality, $\alpha(r)$ is set to 1. The electro-mechanical impulse response $\beta(t)$ describes the spatially-independent bandwidth of the receiving element and system electronics. To model an ideal wide-band response, where $\beta(t)$ has no contribution, $\beta(t)$ can be set to $\delta(t)$.

Image Reconstruction Using Optimization Algorithms

It will be apparent to one of skill in the art that images of tissue can be reconstructed from acquired sensor measurements using optimization algorithms. This involves finding an unknown x that minimizes error between a measured response y and a predicted response $\tilde{y}=Hx$. Here, the system matrix H models the responses that are predicted to be measured for any given image x. Representing the response of a linear system by H generally involves converting continuous equations to discretized matrix form. For example, in an embodiment, H can implement transducers using equation (5) to model an OA system, as described below to represent our model.

To solve x, a general approach involves minimizing a convex optimization problem of the form $$\text{minimize } \|Hx - y\|_2^2 + \vartheta(x) \qquad (9)$$

$$\text{subject to } x \in \mathcal{C}$$

Here, $$\|Hx - y\|_2^2$$

is a fidelity function that matches measured data to the model. The regularization function $\vartheta(x)$ penalizes unwanted solutions, occurring due to noise amplification, which otherwise might minimize (9). It will be apparent to one of skill in the art that different regularization functions can be used depending on anticipated properties of a reconstructed image. Generally, $\vartheta(x)$ has a corresponding proximal operator that can be computed efficiently, as described in the section on Optimization Algorithms below. For example, in $\ell_1$-minimization, $\vartheta(x)$ promotes sparse solutions, with few non-zero elements, by using an $\ell_1$-norm $\|\bullet\|_1$. The $\ell_1$ proximal operator is a simple soft-thresholding function. A preferred embodiment uses total-variation (TV) regularization, which involves a weighted $\ell_1$-norm to enforce sparseness in the spatial gradient of x, promoting image smoothness. This helps to reduce noise when visualizing tissue. In equation (9), the convex set $\mathcal{C}$ represents constraints, restricting the allowed values of x. For example, $\mathcal{C} = \{x | x \geq 0\}$ will permit only non-negative values in x, which is useful when the unknown variable must be positive.

Equation (9) can be solved by several techniques known in the art, including an Alternating Direction Method of Multipliers (ADMM) algorithm and an Accelerated Proximal Gradient (APG) algorithm. Further details of implementing such processes are provided in a section on Optimization Algorithms below.

In an embodiment to perform motion tracking, additional variables representing probe position and orientation must be solved. When these are included, the system matrix H becomes non-linear (with respect to these variables), which makes solving equation (9) more difficult compared to conventional image reconstruction. In this case, Sequential Convex Optimization algorithms can be used to iteratively compute a sequence of linearized convex subproblems, which makes equation (9) more tractable, as further described below.

System Model

Frames Collected by Linear Array

To describe a preferred embodiment of the present invention, a system model (i.e. a computational model of a physical system) is developed by extending equation (4) to multiple frames. This is applicable in 2D clinical imaging, where a hand-held probe with linear transducer array is manually scanned along the surface of a subject's tissue. The probe 700 delivers light through an optical source aperture (e.g. a transparent window) adjacent to the array. In an embodiment, the optical source aperture corresponds to an optical exit port 720. In an embodiment, the probe 700 comprises acoustic receivers 710, such as piezoelectric elements of a linear transducer array. Following illumination by an optical pulse, the array records acoustic responses 750 to capture a frame of data.

In 2D imaging, each frame corresponds with a tissue slice in the probe's imaging plane. FIG. 2 illustrates frames acquired at two alternating wavelengths along the probe's trajectory. In FIG. 2, an optically absorbing volume 705 is shown with multiple 2D slices. This includes a first 2D slice 706 at a first optical wavelength, and a second 2D slice 707 at a second optical wavelength. For each 2D slice, locations of acoustic receivers of a moving linear array are indicated by dots at the surface of the volume.

By extending equation (4), the opto-acoustic signals for the j-th frame are $$y_j(r_l, t) = \int_{\mathbb{R}^3} h(r_l - r, t)\psi_j(r)dr, \qquad (10)$$

where $r_l$ is the position of the l-th transducer element in the probe's local coordinate system, and t is time elapsed since illumination. Since the probe can move, the frame's acoustic source distribution $\psi_j$ is defined relative to the probe's coordinates, and depends on the probe's illumination of tissue. This is equal to $$\psi_j(r) = \eta(\lambda_j, \tau_j(r))\varphi(\lambda_j, r), \qquad (11)$$

where the rotation and translation for each frame are represented using a rigid affine transform function $$\tau_j(r) = A_j r + b_j, \qquad (12)$$

with rotation matrix $A_j$ and translation $b_j$. Thus, $\tau_j$ converts $\eta$ from global coordinates to the probe's local coordinates. In global coordinates, by combining (2) and (3), $\eta$ is given by $$\eta(\lambda_j, r) = \gamma(r)\sum_i m_i(\lambda_j) \chi_i(r), \qquad (13)$$

where $\lambda_j$ is the optical wavelength of the j-th frame. In a dual-wavelength system, $\lambda_j$ sequentially alternates between two different values. Since the optical source aperture moves with the probe, in an embodiment, the light distribution $\varphi$ is assumed to remain stationary in the probe's coordinates.

In an embodiment, each delivered pulse of optical energy and its corresponding acquisition of resulting acoustic responses occur together sufficiently rapidly that these are treated as a single instantaneous event.

Forward Model

In an embodiment, the forward model predicts the data received by the probe. In equations (10) to (13), the opto-acoustic signals responses $y_j$ depend on: i) the volume fraction abundances $\chi_i$, for chromophores $i = 1, \ldots, n_\mu$; and, ii) the probe's orientation $A_j$ and position $b_j$, for frames $j = 1, \ldots, n_f$. In an embodiment, these parameters correspond to inputs in our forward model, but also represent the unknown variables solved during image reconstruction; and, other parameters, $m_i$, $\varphi$ and $\gamma$, are treated as constants that are determined in advance.

Volume fraction abundance of chromophores in tissue. To model the tissue, in an embodiment, it is subdivided into voxels, arranged on a 3D grid. Each voxel is associated with a set of chromophore abundances. The total number of voxels is $n_v = n_x n_y n_z$, where $n_x$, $n_y$ and $n_z$ are the number of voxels along the x-, y- and z-axes. For the i-th chromophore, the volume fraction abundance is represented as a vector $x_i \in \mathbb{R}^{n_v}$. Thus, the tissue can be represented by a matrix variable $X = [x_1, x_2, \ldots, x_{n_\mu}] \in \mathbb{R}^{n_v \times n_\mu}$, where $n_\mu$ is the number of chromophores. For convenience, this is vectorized to $x = \mathrm{vec}(X) \in \mathbb{R}^{n_v n_\mu}$.

System matrix. For a tissue represented by $x \in \mathbb{R}^{n_v n_\mu}$, in an embodiment, the predicted opto-acoustic response signals for the j-th frame are represented by a vector $\tilde{y}_j \in \mathbb{R}^{n_m}$. The number of measurements $n_m$ is equal to the number of transducer channels $n_c$ times the number of samples per channel $n_s$. For each frame, in an embodiment, a system matrix $H_j \in \mathbb{R}^{(n_m) \times (n_v n_\mu)}$ is used to represent the linear discretized operator corresponding to equation (10). Thus, the predicted response is $$\tilde{y}_j = H_j x.$$

In this model, the matrix operator $H_j$, which is composed of four components, is defined as $$H_j = H_0 \Phi_{\lambda_j} T_{p_j} M_{\lambda_j}, \tag{14}$$

where $M_{\lambda_j} \in \mathbb{R}^{(n_v) \times (n_v n_\mu)}$ is the absorption matrix for wavelength $\lambda_j$, which contains optical absorption coefficients of each chromophore; $T_{p_j} \in \mathbb{R}^{n_v \times n_v}$ is the transformation matrix for the configuration vector $p_j \in \mathbb{R}^{n_p}$, which describes probe position and orientation; $\Phi_{\lambda_j} \in \mathbb{R}^{n_v \times n_v}$ is the optical illumination matrix for wavelength $\lambda_j$, describing the radiant fluence distribution; and, $H_0 \in \mathbb{R}^{n_m \times n_v}$ is the acoustic response matrix. These are described below.

To compute signal responses from multiple frames, in an embodiment, the overall system matrix $H \in \mathbb{R}^{(n_m n_f) \times (n_v n_\mu)}$ is given by $$H = \begin{bmatrix} H_1 \\ H_2 \\ \vdots \\ H_{n_f} \end{bmatrix}. \tag{15}$$

Thus, we can write $$\tilde{y} = H x, \tag{16}$$

where $\tilde{Y} = [\tilde{y}_1, \tilde{y}_2, \ldots, \tilde{y}_{n_f}] \in \mathbb{R}^{n_m \times n_f}$ and $\tilde{y} = \mathrm{vec}(\tilde{Y})$.

Absorption matrix ($M_{\lambda_j}$). To derive $M_{\lambda_j}$, equation (13) is used. In an embodiment, it is assumed that each chromophore index $i \in \{1, \ldots, n_\mu\}$ has a known absorption coefficient $m_i(\lambda_j)$ at the wavelength index $\lambda_j \in \{1, \ldots, n_\lambda\}$. The optical absorption vector $m_{\lambda_j} \in \mathbb{R}^{n_\mu}$ at wavelength $\lambda_j$ is defined as $$m_{\lambda_j} = [m_1(\lambda_j), m_2(\lambda_j), \ldots, m_{n_\mu}(\lambda_j)]^T. \tag{17}$$

Accordingly, the optical absorption matrix for (14) is $$M_{\lambda_j} = \tilde{m}_{\lambda_j}^T \otimes I_{n_v}, \tag{18}$$

where $\tilde{m}_{\lambda_j} = \gamma_0 m_{\lambda_j}$. This has a simple interpretation, which is that equation (18) replicates $m_{\lambda_j}$ for each voxel and multiplies by $\gamma_0$.

Transformation matrix ($T_{p_j}$). In each frame, the probe has a different position and orientation. The rotation matrix $A_j \in \mathbb{R}^{3 \times 3}$ and the translation $b_j \in \mathbb{R}^3$ of equation (12) can be generated by a list of parameters $p_j \in \mathbb{R}^{n_p}$ called the configuration. There is some flexibility in how $A_j$ and $b_j$ are generated from the configuration, depending on the permitted probe motions. The number of parameters $n_p$ is equal to the degrees of freedom. In an embodiment, the configuration $p_j = (\theta_j, b_j)$ is used, which has six parameters: the three translations for $b_j$, and three Euler angles $\theta_j \in \mathbb{R}^3$ to represent roll, pitch and yaw. The rotation matrix is $$A_j = R_1(\theta_{j,1}) R_2(\theta_{j,2}) R_3(\theta_{j,3}), \tag{19}$$

where $R_1$, $R_2$ and $R_3$ represent rotations about the three coordinate axes. In an embodiment, it may be desired to implement fewer degrees of freedom for the trajectory. In this case, if fewer degrees of freedom are required, then any of the configuration parameters can be replaced with constants to constrain the trajectory.

In an embodiment, the transformation matrix $T_{p_j} \in \mathbb{R}^{n_v \times n_v}$ for (14) is defined as a matrix operator that transforms voxels in $\mathbb{R}^{n_v}$ according to the configuration $p_j$. In other words, $T_{p_j}$ applies $A_j$ and $b_j$ to each voxel in an image. This (inversely) rotates and translates the tissue so it is situated in the local coordinate frame of the probe. In practice, the matrix $T_{p_j}$ can be implemented efficiently, in an embodiment, using a custom function on a CPU or GPU.

Optical illumination matrix ($\Phi_{\lambda_j}$). In a preferred embodiment for the modeled physical system, light is delivered by an optical aperture that remains stationary in the probe's local coordinates (whereby it moves relative to global coordinates). Thus, for wavelength $\lambda_j$, it may be assumed the fluence profile $\varphi$ remains fixed relative to the probe. This permits pre-computing $\Phi$ once per wavelength, rather than solving it at each probe position. In an embodiment, this represents and approximation that assumes tissue heterogeneities and deformation that impact $\varphi$ are negligible. According to equation (1), the optical illumination matrix $\Phi_{\lambda_j} \in \mathbb{R}^{n_v \times n_v}$ applies a matrix diagonal weighting, corresponding to pointwise multiplication of each voxel. Thus, $\Phi_{\lambda_j} = \mathrm{diag}(\varphi_{\lambda_j})$, where $\varphi_{\lambda_j} \in \mathbb{R}^{n_v}$ is a vector representing the fluence profile. This is governed by the radiation transport equation, as apparent to one of skill in the art, and can be determined in several ways, including diffusion approximations, finite-element models, or Monte Carlo based methods. In a preferred embodiment, analytic expressions are implemented based on a diffusion approximation, which can be tuned for optical properties of a desired tissue (e.g. breast tissue).

Acoustic response matrix ($H_0$). In a preferred embodiment, the acoustic response matrix $H_0 \in \mathbb{R}^{n_m \times n_v}$ implements equation (5) in linear discretized form, as described below.

Separable Operator for Linear Array

It has been demonstrated that a mathematical operator corresponding to equations (10) to (12) is separable, as described in "Fast 3-D Opto-Acoustic Simulation for Linear Array with Rectangular Elements," by Zalev et al., IEEE Trans. Ultrasonics, Ferroelectrics, and Frequency Control, Vol. 68, No. 5, May 2021, at pp. 1885-1906, which is incorporated herein by reference. For each transducer, such an approach implements the spherical volume integration of equations (4) to (6) to model acoustic wave propagation in a more efficient manner. By generalizing this to matrix form, in an embodiment, the acoustic response matrix $H_0 \in \mathbb{R}^{n_m \times n_v}$ can be represented as the product of two matrices. This is written $$H_0 = F_0 G_0. \tag{20}$$

Here, the matrix factor $F_0 \in \mathbb{R}^{n_m \times n_{m'}}$ acts on the probe's 2D imaging plane. The factor $G_0 \in \mathbb{R}^{n_{m'} \times n_v}$ acts along planes perpendicular to it, spanning a 3D volume. In this sense, $F_0$ and $G_0$ are matrix co-factors of each other with respect to the separability of $H_0$.

In an embodiment, by representing (20) as sparse matrices, the separable form permits higher computational efficiency because $H_0$ is non-factorized and less sparse than $F_0$ and $G_0$. In general, the performance improvement for factorized sparse matrices is similar to the case for discretized analytic equations because the sparsity pattern yields substantially the same number of operations either way.

In an embodiment, separability is applied to the overall system matrix H of equation (15). By substituting (20) into (14), for frame j, we have $$H_j = \underbrace{F_0 G_0 \Phi_{\lambda_j} T_{p_j} M_{\lambda_j}}_{G_j}, \tag{21}$$

where $G_j$ is defined as $$G_j = G_0 \Phi_{\lambda_j} T_{p_j} M_{\lambda_j}. \tag{22}$$

Accordingly, (15) can be written as $$H = FG, \tag{23}$$

where the overall separable factors F and G are $$F = F_0 \otimes I_{n_f} = \begin{bmatrix} F_0 & 0 & \cdots & 0 \\ 0 & F_0 & \cdots & 0 \\ \vdots & \vdots & \ddots & \vdots \\ 0 & 0 & \cdots & F_0 \end{bmatrix}, \tag{24}$$

and

12

-continued $$G = \begin{bmatrix} G_1 \\ G_2 \\ \vdots \\ G_{n_f} \end{bmatrix}. \tag{25}$$

The separable form of equation (23) (instead of performing a volume integration that encounters each voxel for every transducer), reduces the computational complexity of each frame from $\mathcal{O}(n^3)$ to approximately $\mathcal{O}(n^2)$, where $n^3 = n_v$ is the number of voxels in a 3D image (assuming the number of transducers $n_c \approx n$). For a 3D image with dimensions $100 \times 100 \times 100$, this represents 100 times computational savings, compared to a non-separable approach.

Figure 4:
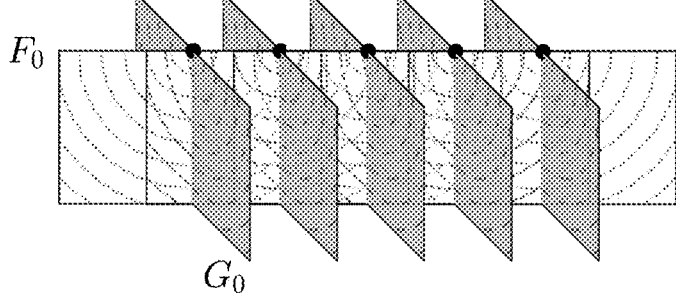
FIG. 4 is illustrative of matrix factors of a separable acoustic response matrix.

FIG. 4 is illustrative of a response matrix $H_0 = F_0 G_0$ that is split into two stages to improve computational efficiency for a linear array, instead of directly implementing a spherical volume integration of equation (5). As shown, to model time-domain signals for all transducer elements (black dots), the matrix factor $F_0$ performs integration (summation) along arcs that span a 2D plane (white), corresponding to a cross-sectional slice of tissue. The slice is generated by the matrix factor $G_0$, which performs integration along independent perpendicular planes (gray), spanning the 3D volume. Since the transducer elements are co-linear, all signals in $F_0$ require the same planes from $G_0$ (repeated at consecutive offsets as shown), so intermediate data can be shared. Thus, by splitting $H_0$ into factors $F_0$ and $G_0$, redundant computation is eliminated.

---

Algorithm 1 two-stage iterative 3D opto-acoustic image reconstruction

Input: $y = (y_1, \ldots, y_{n_f}) \in \mathbb{R}^{n_f n_m}$
Output: $x \in \mathbb{R}^{n_v n_\mu}$
Require: $F_0 \in \mathbb{R}^{n_{nm} \times n'}$, $G = (G_1, \ldots, G_{n_f}) \in \mathbb{R}^{n_f n_m' \times n_v n_\mu}$, $\vartheta : \mathbb{R}^{n_v n_\mu} \to \mathbb{R}$, $\rho \in \mathbb{R}^+$
1: function TWOSTAGERECONSTRUCT($y_1, \ldots, y_{n_f}$)
2:    $x^{(0)} \leftarrow 0, u^{(0)} \leftarrow 0$      ▷ initialize x and u
3:    for n = 0 ... $n_{max} - 1$ do
4:      for j = 1 ... $n_f$ do
5:        $z_j^{(n+1)} \leftarrow \text{RECONSTRUCT2D}(y_j, G_j x^{(n)} + u_j^{(n)})$    ▷ 2D reconstruction for each slice
6:      end for
7:    $z^{(n+1)} \leftarrow \left(z_1^{(n+1)}, z_2^{(n+1)}, \ldots, z_{n_f}^{(n+1)}\right)$
8:    $x^{(n+1)} \leftarrow \text{RECONSTRUCT3D}(z^{(n+1)} - u^{(n)})$    ▷ reconstruct 3D volume using all slices
9:    for j = 1 ... $n_f$ do
10:      $u_j^{(n+1)} \leftarrow u_j^{(n)} + \left(G_j x^{(n+1)} - z_j^{(n+1)}\right)$    ▷ update dual variables
11:    end for
12:    $u^{(n+1)} \leftarrow \left(u_1^{(n+1)}, u_2^{(n+1)}, \ldots, u_{n_f}^{(n+1)}\right)$
13:    end for
14:    return $x^{(n+1)}$
15: end function
16: function RECONSTRUCT2D ($y_0, u_0$)
17:    return $\underset{z_0}{\text{argmin}} \left\{\|F_0 z_0 - y_0\|_2^2 + \frac{\rho}{2}\|u_0 - z_0\|_2^2\right\}$
18: end function
19: function RECONSTRUCT3D($\bar{z}$)

-continued

| Algorithm 1 two-stage iterative 3D opto-acoustic image reconstruction |
|---|

20:    $\text{return } \underset{x}{\arg\min}\left\{\frac{\rho}{2}\|Gx - z\|_2^2 + \vartheta(x)\right\}$     ▷ 3D volumetric recontruction of chromophores 21: end function

Image Reconstruction and Motion Tracking
Image Reconstruction

In an embodiment, image reconstruction using the separable operator described above is performed by substituting (15) into (9) to obtain the convex optimization problem $$\underset{x}{\text{minimize}} \; \|FGx - y\|_2^2 + \vartheta(x) \qquad (26)$$

$$\text{subject to } x \in C$$

Here x represents the volume fraction abundances of the tissue chromophores, which have non-negative values. Accordingly, a preferred embodiment specifies $C$ with x≥0. To solve (26), in an embodiment, a minimization algorithm that requires a proximal operator of the indicator function $\mathcal{I}_C$ is used to confine x to $C$. This corresponds to a replacement of negative values with zero after each iteration, as would be apparent to one of skill in the art. If desired, additional constraints can be used, such as ensuring the volume fractions sum to less than one, consistent with physical principles. In an embodiment, other constraints as used in optimization-based spectral unmixing are possible, as would be apparent to one of skill in the art.

In an embodiment, computing an image comprises minimization of error between received acoustic responses y and predicted acoustic responses FGx in accordance with minimization process of equation (26), as described herein, where computing a system matrix H comprises: applying a matrix factor G to an image variable x to produce intermediate slices; and applying a matrix co-factor F to intermediate slices to produce, at least in part, predicted acoustic responses.

When solving (26), a preferred embodiment uses a regularization function $\vartheta$ that includes isotropic TV as well as $\ell_1$-minimization. For example, this can be $$\vartheta(x) = \alpha_1\|x\|_1 + \alpha_2\sum_{i=1}^{n_\mu}\|Dx_i\|_{2,1}, \qquad (27)$$

where $\alpha_1$ and $\alpha_2$ are regularization parameters, and $D=(D_x, D_y, D_z)\in \mathbb{R}^{(3\times n_v)\times n_v}$ is a linear matrix operator for TV regularization that computes spatial gradients in the x, y and z directions. Here, D is applied to each chromophore $x_i$. In equation (27), the $\|\bullet\|_{2,1}$ group-norm has a dual-proximal operator that facilitates using isotropic TV with 3D volumes. Minimizing this type of equation can be performed efficiently with dual-proximal methods, as will be apparent to those of skill in the art, as further described in the section on Optimization Algorithms below. In an alternate embodiment, this can be achieved with similar approaches involving primal-dual optimization. In other embodiments, anisotropic TV can be implemented by using the $\ell_1$-norm $\|\bullet\|_1$ in (27) instead of $\|\bullet\|_{2,1}$, which may reduce visual performance, but is computationally simpler.

Two-Stage Iterative 3D Opto-Acoustic Image Reconstruction

To improve computation of equation (26), in an embodiment, a two-stage iterative 3D reconstruction is proposed, where separable parts are solved independently. The sequence, which is performed iteratively, involves first reconstructing a monochrome (single-wavelength) 2D slice for each frame, followed by 3D volumetric reconstruction of chromophores.

Using the separable operator described above, in an embodiment, equation (26) is split into two parts. From (21) and (22), when $H_j$ is applied to x, we can write $$H_j x = F_0 \underbrace{G_j x}_{z_j} = F_0 x_j, \qquad (28)$$

where $z_j \in \mathbb{R}^{n_{m'}}$ is a new variable, defined by $$z_j = G_j x. \qquad (29)$$

We write $Z=[z_1, \ldots, z_{n_f}]\in \mathbb{R}^{n_m \times n_f}$ and z=vec(Z). Thus, for the overall system matrix, $$Hx=FGx=Fz, \qquad (30)$$

where Gx=z. Using this substitution, equation (26) becomes $$\underset{x,z}{\text{minimize}} \; \|Fz - y\|_2^2 + \vartheta(x) \qquad (31)$$

$$\text{subject to } z = Gx,$$

| Algorithm 2 opto-acoustic image reconstruction with solving motion |
|---|

Input: $y = (y_1, \ldots, y_{n_f}) \in \mathbb{R}^{n_f p_{tm}}$
Output: $x \in \mathbb{R}^{n_v n_u}$, $p \in \mathbb{R}^{n_p n_f}$
  1:  procedure RECONSTRUCTIONANDTRACKING(y)
  2:    $x^{(0)} \leftarrow 0, p^{(0)} \leftarrow 0$           ▷ initialize x and p
  3:    for k = 0 . . . $k_{max}$ − 1 do
  4:      for j = 1 . . . $n_f$ do -continued

| Algorithm 2 opto-acoustic image reconstruction with solving motion | |
|---|---|
| 5:  $H_{p_j}^{(k)} \leftarrow H_0 \Phi_{\lambda_j} T_{p_j}^{(k)} M_{\lambda_j}$ | ▷ update the system response of frame j from (14) |
| 6:  $J_{p_j}^{(k)} \leftarrow \dfrac{\partial H_{p_j}^{(k)} x^{(k)}}{\partial p_j} \mid_{p_j^{(k)}}$ | ▷ update Jaccobian of frame j |
| 7:   end for | |
| 8:  $\left(x^{(k+1)}, \Delta p^{(k+1)}\right) \leftarrow \underset{(x,\Delta p) \in C_k}{\operatorname{argmin}} \left\{ \left\| H_p^{(k)} x + J_p^{(k)} \Delta p - y \right\|_2^2 + \vartheta(x) \right\}$ | ▷ solve x and $\Delta p$ |
| 9:  $p^{(k+1)} \leftarrow p^{(k)} + \Delta p^{(k+1)}$ | ▷ update p from (33b) |
| 10:   end for | |
| 11:  end procedure | | where the constraint $x \in C$ is omitted for clarity.

Equation (31) can be solved with an ADMM splitting algorithm, as described in the section on Optimization Algorithms below. The result obtained by applying equation (31) to equation (41) is presented as Algorithm 1. An interesting interpretation of Algorithm 1 is that there is an intermediate variable $z_j$ for each frame, corresponding to a monochrome 2D reconstructed image. Each reconstructed $z_j$ requires no inherent positional information, since it is in the probe's local coordinates. Algorithm 1 performs an outer loop, with two separate inner minimizations. First, the algorithm reconstructs a 2D image $z_j$ for each frame. Then, once $z_j$ is formed for all frames, the 3D volume x is reconstructed from the intermediate variables, using each frame's position and orientation. Since the positional information is not required until the second stage, a motion trajectory can be solved using data computed from the first stage, as described below.

Image Reconstruction Combined with Solving Motion

Solving motion of a trajectory is developed from equation (9), using the system matrix H of equation (15), which depends on the configuration parameters $p=(p_1, \ldots, p_{n_p})$ that describe the probe orientation and position for each frame. To highlight the non-linear dependence of H on p, the system matrix is rewritten with modified notation as $H \equiv H_p$. To simultaneously perform reconstruction of x, while determining probe configuration p, it is desirable to solve $$\underset{(x,p) \in C}{\operatorname{minimize}} \|H_p x - y\|_2^2 + \vartheta(x) \qquad (32)$$

However, due to the form of $H_p$, which is non-linear in p, equation (32) is not convex, which makes finding a solution more computationally difficult.

To convert (32) to a form that can be solved, a linear approximation to $H_p$ around an initial estimate of p is used. For an incremental change in configuration parameters $\Delta p \in \mathbb{R}^{(n_p n_f)}$, the linear approximation is $$H_{(p+\Delta p)} \approx H_p + J_p \Delta p,$$

where $$J_p = \frac{\partial}{\partial p}(H_p x) \in \mathbb{R}^{n_m \times (n_p n_f)}$$

represents the Jaccobian derivative of $H_p$ at x with respect to each parameter in p. In an embodiment, the Jaccobian derivative $J_p$ is stored as a matrix of values. This permits iteratively solving a relaxed approximation to (32), where each iteration is a two step process. Such a two step approach is known in the art as sequential convex optimization. At the k-th iteration, first, solutions for $x^{(k+1)}$ and $\Delta p^{(k+1)}$ are simultaneously solved. Then, $p^{(k+1)}$ is solved by incrementally updating $p^{(k)}$ with $\Delta p^{(k+1)}$.

Thus, in an embodiment, each iteration comprises the following two steps:

Step 1:

$$\begin{bmatrix} x^{(k+1)} \\ \Delta p^{(k+1)} \end{bmatrix} = \underset{(x,\Delta p) \in C_k}{\operatorname{argmin}} \left\{ \|H_p^{(k)} x + J_p^{(k)} \Delta p - y\|_2^2 + \vartheta(x) \right\} \qquad (33a)$$

Step 2:

$$p^{(k+1)} = p^{(k)} + \Delta p^{(k+1)} \qquad (33b)$$

This is illustrated in Algorithm 2.

To constrain for constant velocity motion estimation, in an embodiment, $C_k$ can project $p^{(k)}$ onto a linear trajectory along the probe's elevational axis after each iteration using robust fitting.

Figures 8, 9:
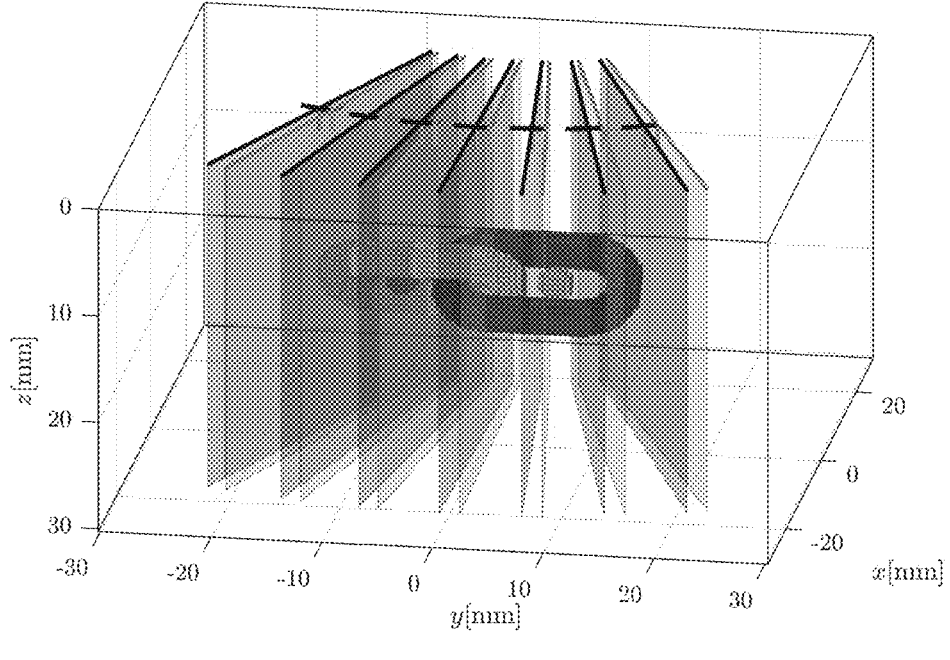
FIG. 8 is illustrative of a trajectory of frames used in simulating acoustic signals of a 3D volume comprising a digital phantom.
FIG. 9 is illustrative of a reconstructed 3D volume generated from acoustic data of the digital phantom shown in FIG. 8.

A reconstructed image of the 3D volume illustrated in FIG. 8 is shown in FIG. 9.

Efficient Implementation of Reconstruction and Solving Motion

Figure 3:
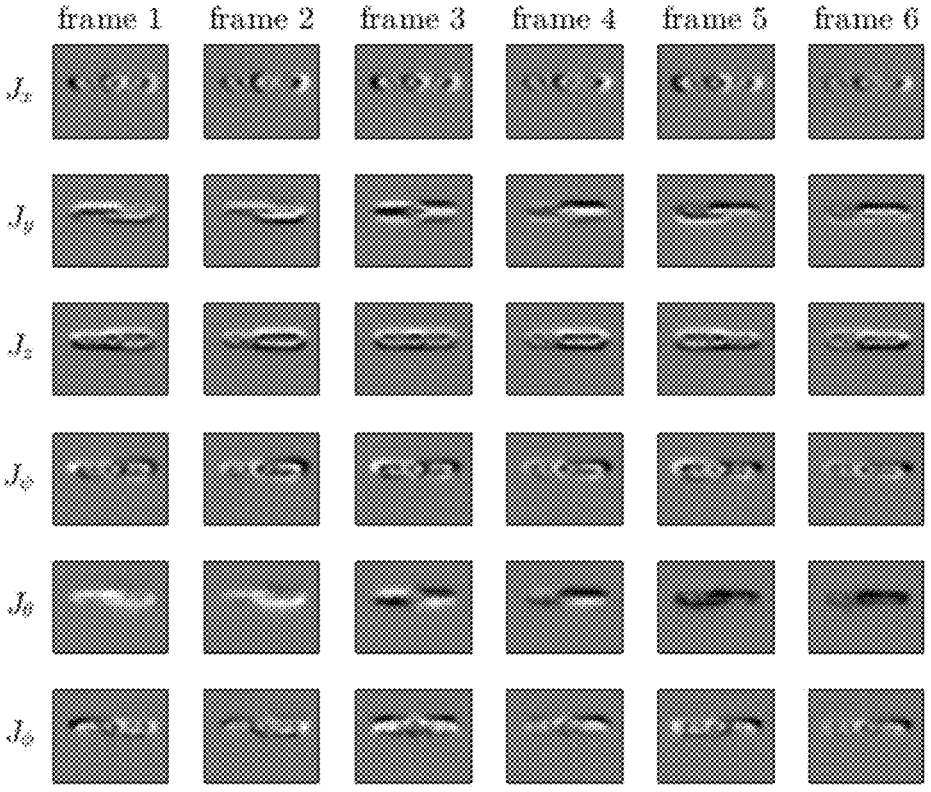
FIG. 3 is illustrative of data for a Jacobian matrix obtained during a reconstruction with solving motion.

In an embodiment, by combining the separability described above with Algorithm 2, additional advantages can be achieved. For example, when a 2D slice is separately reconstructed using data from each frame, this can be used to determine an initial estimate of motion along the lateral axis of the probe. We modify equation (31) into a split form similar to equation (33a). The split form permits applying the Jacobian matrix $J_p$ in the 2D image-domain of z, rather than in the time-domain of measurement data y, which leads to a more efficient implementation. FIG. 3 illustrates $J_p$ computed in this 2D image-domain, where the values for the matrix are shown graphically. With these modifications, an embodiment for the implementation of Step 1 becomes $$\text{minimize}_{x,z,\Delta p} \ \|Fz - y\|_2^2 + \vartheta(x) \qquad (34)$$

$$\text{subject to } z = G_p^{(k)}x + J_p^{(k)}\Delta p,$$

$$x \geq 0,$$

where $\vartheta(x)$ is the same as equation (27).

As described in the section on Optimization Algorithms below, a TFOCS algorithm performs minimization using first-order iterations with an accelerated proximal gradient (APG) method.

In an embodiment, optimization algorithm objective functions can be converted to a block-composite form (BCF), which is described in equation (42). However, to solve a problem in BCF form, it is convenient to use its dual form, described in equation (43). In an embodiment, to represent equation (34) in BCF form, we use a primal variable $v=(z, x, \Delta p)$.

The result is illustrated in Algorithm 3, which combines Algorithm 1 with Algorithm 2.

In Algorithm 3, at the k-th (outer) iteration, the block-composite system matrix $L^{(k)}$ is $$L^{(k)} = \begin{bmatrix} -1 & G_p^{(k)} & J_p^{(k)} \\ F & 0 & 0 \\ D & 0 & 0 \\ 1 & 0 & 0 \end{bmatrix}, \qquad (35)$$

where D is the linear operator for TV regularization, as used in equation (27). The offset constant for (42) is $c=(0, y, 0, 0)$.

To encode (34), the function map $\xi=[\mathcal{I}_0, \|\cdot\|_2, \|\cdot\|_{2,1}, \|\cdot\|_1]$ is used, which implements $\vartheta(x)$ and $\mathcal{I}_0$ encodes the equality constraint. The positivity constraint is encoded by $\xi_0$. The proximal operator $prox_{\xi_0}(v)$ and dual-proximal operator $prox_{\xi*}(u)$, which are required in equation (43), are $$prox_{\xi_0} = \begin{bmatrix} prox_{\mathcal{I}_{\mathbb{R}_+^n}} \\ prox_{\mathcal{I}_{\mathbb{R}_+^n}} \\ prox_{\mathcal{I}_{\mathbb{R}^n}} \end{bmatrix}, \ prox_{\xi*} = \begin{bmatrix} prox_{\ell_2} \\ prox_{\mathcal{I}_{\mathbb{R}^n}} \\ prox_{\ell_{2,\infty}}(\alpha_2) \\ prox_{\ell_\infty}(\alpha_1) \end{bmatrix}. \qquad (36)$$

Here, the function $$prox_{\mathcal{I}_{\mathbb{R}_+^n}}$$

represents projection into the positive halfspace $$\mathbb{R}_+^{(n)},$$

which implements the constraint $x \geq 0$, replacing negative values with zero. The unconstrained primal constraints are represented by projection into $\mathbb{R}^n$ using $prox_{\mathcal{I}_{\mathbb{R}^n}}$. For $prox_{\xi*}$, the remaining terms in equation (34) are converted to dual form. The $\ell_2$-norm $\|\cdot\|_2$ is self-dual, so its dual-proximal operator is $prox_{\ell_2}$. Implementing the $\ell_1$ minimization term in $\vartheta(x)$ involves its dual, $prox_{\ell_\infty}$. The dual for the $\|\cdot\|_{2,1}$ group-norm in (27) is $prox_{\ell_{2,\infty}}$. The constants $\alpha_1$ and $\alpha_2$ correspond to the regularization parameters in (27).

In Algorithm 3, at iteration k, the Jacobian matrix $$J_p^{(k)}$$

can be computed, in an embodiment, by finite difference with respect to changes in $p^{(k)}$. For illustration, Figure FIG. 3 shows $J_p$, computed in the 2D image domain of z, obtained from a digital phantom as shown in FIG. 8 using 6 frames. When solving equation (34), since the image x is initially unknown, in an embodiment, $$J_p^{(0)}$$

is initialized to zero and updated each iteration.

Figure 10:
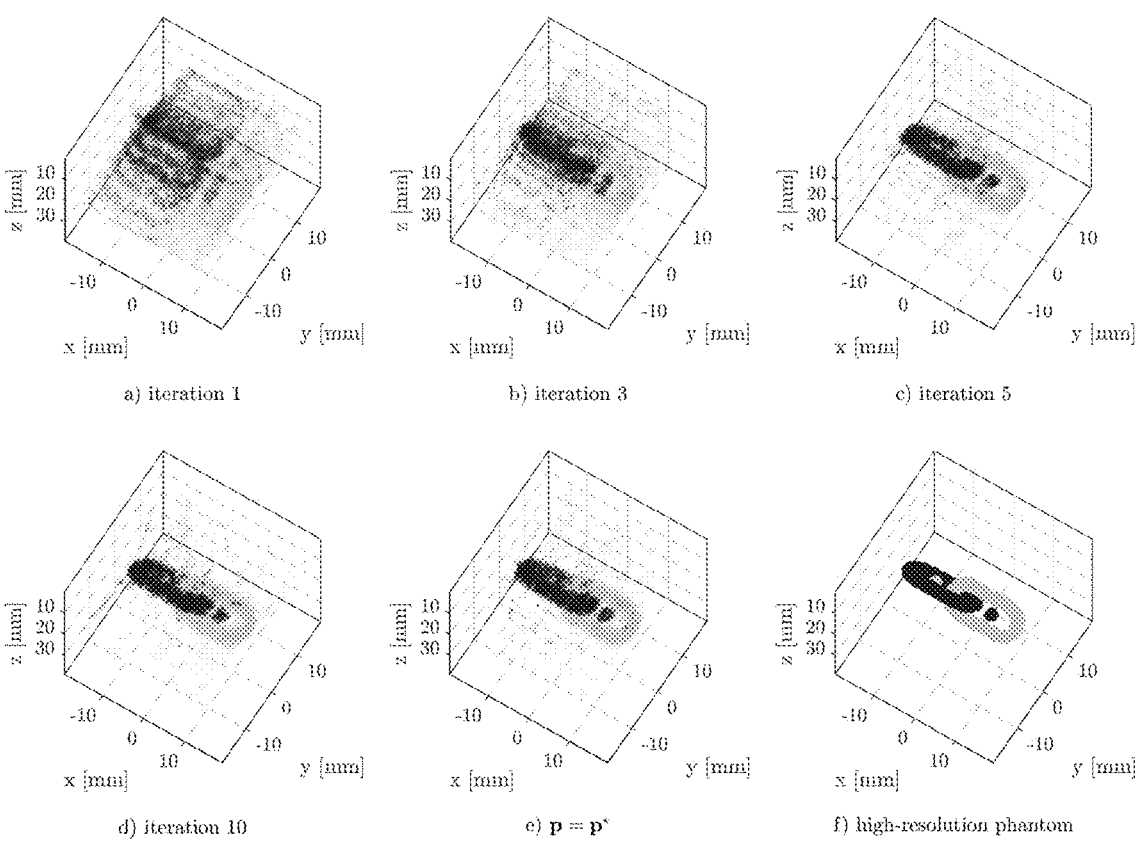
FIG. 10 is illustrative of 3D reconstruction preformed while solving probe motion using Algorithm 3.

Algorithm 3 is demonstrated in FIG. 10. For testing purposes, a dataset was obtained from a digital phantom by simulating of received acoustic signals for probe motion at constant velocity of 15 mm/s along an elevational axis aligned

---

Algorithm 3 Alternate implementation of image reconstruction with solving motion

---

Input: $y = (y_1, \ldots, y_{n_f}) \in \mathbb{R}^{n_f n_m}$, $x^{(0)} \in \mathbb{R}^{n_v n_\mu}$, $p^{(0)} \in \mathbb{R}^{n_f n_p}$ Output: $x \in \mathbb{R}^{n_v n_\mu}$, $p \in \mathbb{R}^{n_f n_p}$ 1:   procedure RECONSTRUCTIONANDTRACKING($y$, $x^{(0)}$, $p^{(0)}$)

2:      $z^{(0)} \leftarrow 0$                      ▷ initialize z, x and p

3:      $\xi \leftarrow [\mathcal{I}_0 \quad \|\cdot\|_2 \quad \|\cdot\|_{2,1} \quad \|\cdot\|_1]$ 4:      for $k = 0 \ldots k_{max} - 1$ do 5:      $\begin{bmatrix} z^{(k+1)} \\ x^{(k+1)} \\ \Delta p^{(k+1)} \end{bmatrix} \leftarrow \text{argmin}_{(z,x,\Delta p) \in C_k} \left\{ \xi \left( \begin{bmatrix} -1 & G_p^{(k)} & J_p^{(k)} \\ F & 0 & 0 \\ D & 0 & 0 \\ 1 & 0 & 0 \end{bmatrix} \begin{bmatrix} z \\ x \\ \Delta p \end{bmatrix} - \begin{bmatrix} 0 \\ y \\ 0 \\ 0 \end{bmatrix} \right) \right\}$    ▷ solve      Eq. (34)

6:      $p^{(k+1)} \leftarrow p^{(k)} + \Delta p^{(k+1)}$                  ▷ update trajectory 7:      end for 8:   end procedure

--- with the y-coordinate of the phantom. The simulation included illumination that alternated between 757 nm and 1064 nm optical wavelengths. A non-uniform pulse sequence was used with a 50 ms delay after the 757 nm wavelength and a 150 ms delay after the 1064 nm wavelength. A total of 14 frames were acquired at an average frame rate of 10 Hz.

In FIG. 10, the reconstructed volume $x^{(k)}$ has 64×64×64 voxels for each chromophore, where k represents the outer iteration count. The reconstruction uses a grid spacing 0.6 mm/voxel. Using Algorithm 3, there were 10 outer iterations performed, and each used 80 inner iterations. The variables $x^{(k)}$ and $p^{(k)}$ were stored after each outer iteration k. An initial velocity estimate of 25 mm/s was specified.

The results in FIG. 10 reveal the evolution of $x^{(k)}$ after k iterations. As $p^{(k)}$ becomes more accurate, the reconstructed 3D image improves. FIG. 10A shows the $x^{(1)}$ reconstruction, generated after the $1^{st}$ outer iteration, using initial position estimate $p^{(0)}$. FIG. 10B shows the $x^{(3)}$ reconstruction after the $3^{rd}$ outer iteration; FIG. 10C shows the $x^{(5)}$ reconstruction after the $5^{th}$ outer iteration; and, FIG. 10D shows the $x^{(10)}$ reconstruction after the $10^{th}$ outer iteration. FIG. 10E shows reconstruction with a single outer iteration when probe position p is initially set to ground truth p*. FIG. 10F shows the ground truth x* used to simulate measured acoustic waves, which has a denser grid geometry (128× 128×128 voxels) compared to the reconstructed image.

Method for Image Reconstruction with Solving Motion

The present invention includes a method for opto-acoustic imaging and solving a motion trajectory of a probe. In an embodiment, the probe comprises acoustic receivers 710 (e.g. acoustic transducers) to receive acoustic responses 750 (a.k.a. acoustic signals); and, an optical exit port 720 (e.g. optical window) to deliver optical energy 730 (e.g. light).

Figure 11:
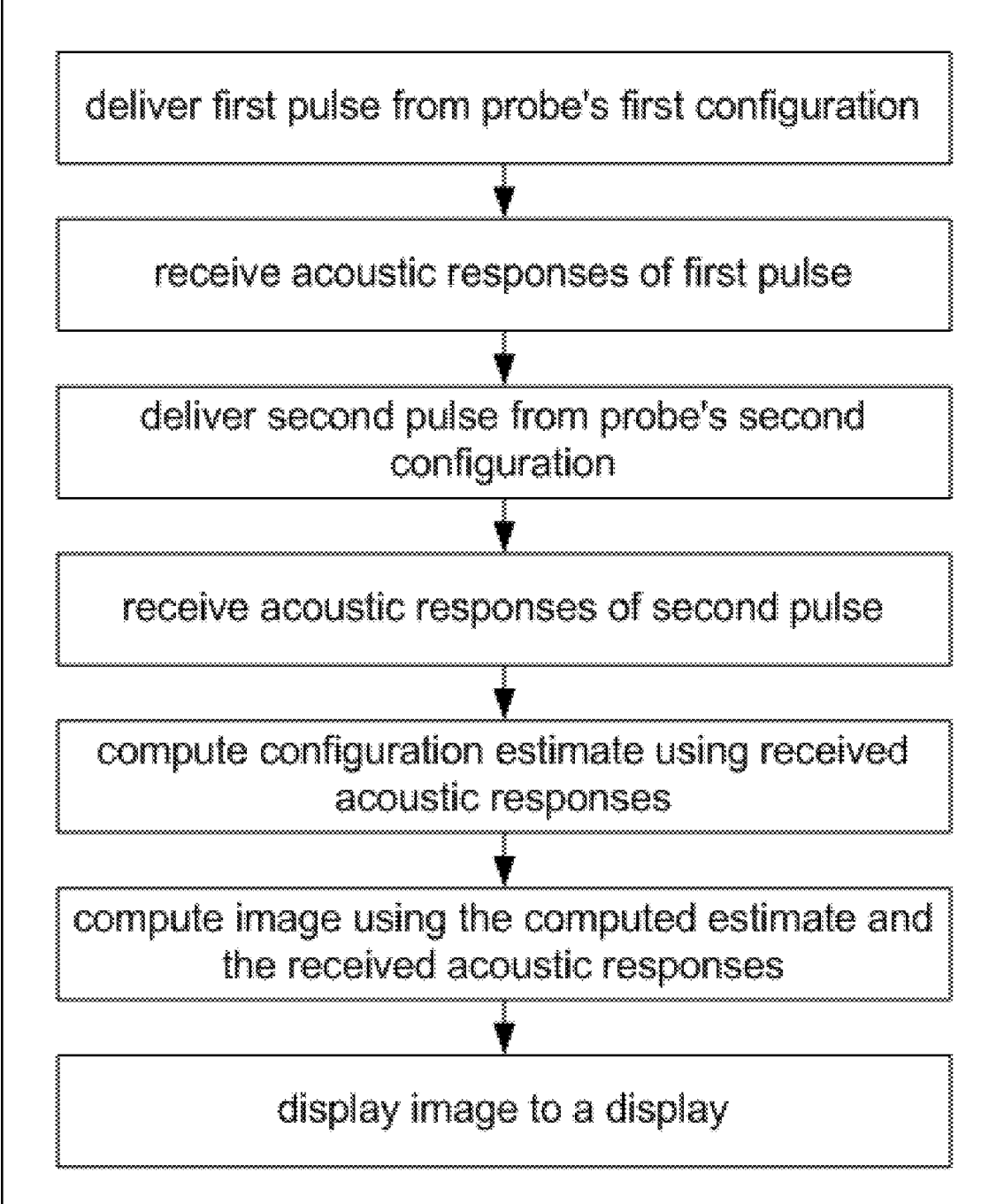
FIG. 11 is a flow diagram illustrating a process flow for image reconstruction with solving motion in accordance with an embodiment.
Figure 12:
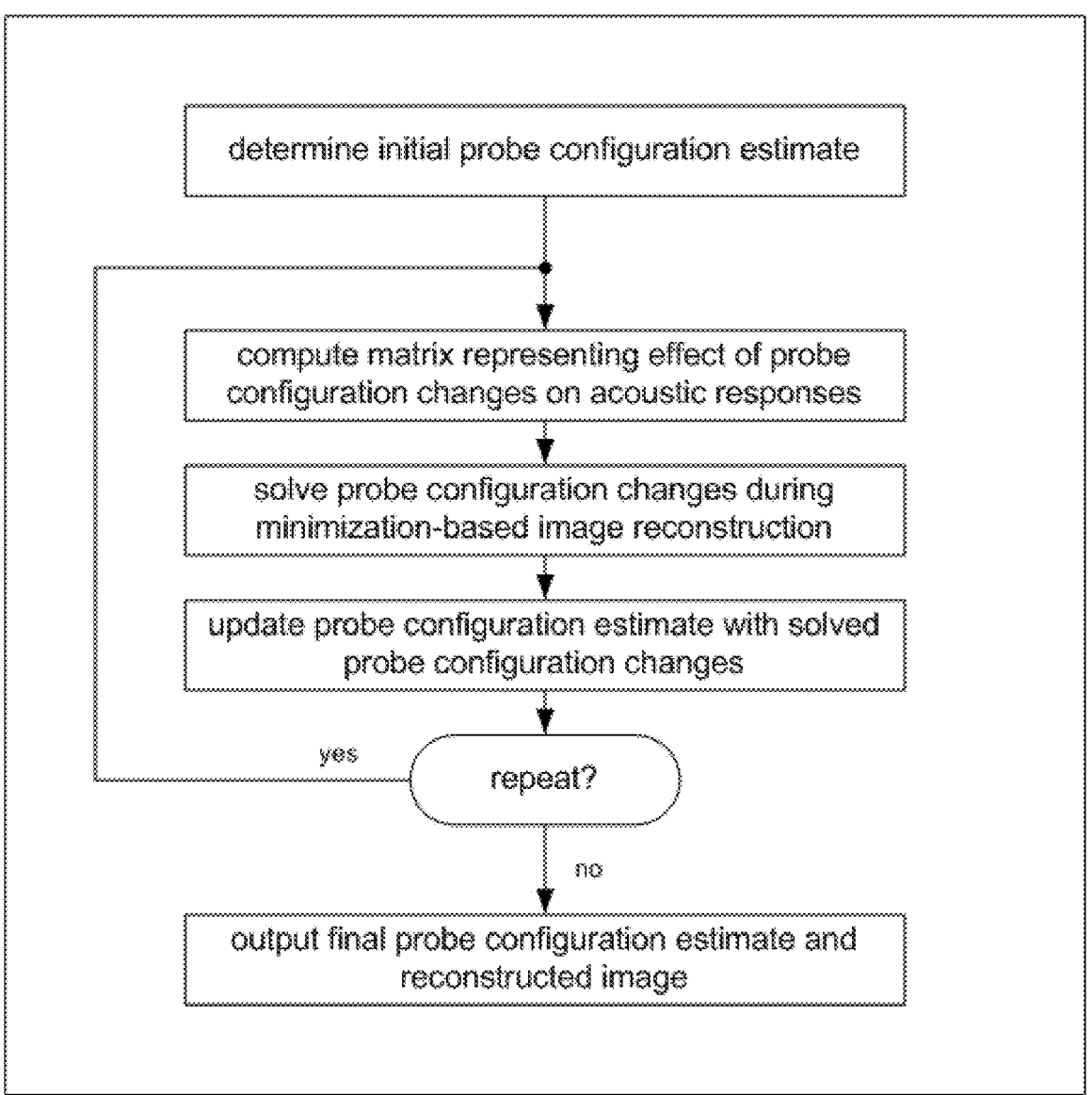
FIG. 12 is a flow diagram illustrating a process flow for iteratively determining probe configuration estimates during minimization-based image reconstruction in accordance with an embodiment.

FIG. 1 is illustrative of a probe 700 with an initial configuration during a first acquisition (acquisition 1) and a different configuration during a second acquisition (acquisition 2). FIG. 11 is a flow diagram illustrating a process flow of an embodiment of image reconstruction with solving a motion trajectory. FIG. 12 is a flow diagram illustrating a process flow of an embodiment for computing a configuration estimate during image reconstruction.

In an embodiment, images are computed by minimizing error between a measured response (received by the probe's transducers) and a predicted response (generated by simulation from a reconstructed image and a probe's rigid body configuration). Generating the predicted response may include applying a system matrix (system response matrix) to an image. This also may include a matrix (e.g. Jacobian derivative matrix) to represent changes of the predicted response due to changes in probe motion (e.g. effects due to a linearized approximation motion for the predicted response). In an embodiment, a probe's configuration includes its position and its orientation. In an embodiment, a probe's configuration comprises a probe position. In an embodiment, a probe's configuration comprises a probe orientation. In an embodiment, an optically absorbing volume 705 comprises at least one optical absorber 740.

In an embodiment, a method for imaging and motion tracking of a probe comprises the steps of: delivering a first pulse of optical energy 731 to a volume 705 from a first position-and-orientation 791 (i.e. configuration) of the probe; receiving first acoustic response 751 due to the first pulse; delivering a second pulse of optical energy 732 to the volume from a second position-and-orientation 792 (i.e. second configuration) of the probe; receiving second acoustic response 752 due to the second pulse; and computing an estimate of the first position-and-orientation 791 relative to the second position-and-orientation 792 using said acoustic responses of both the first and second pulses.

In an embodiment, the method further comprises the steps of: computing an image of the volume using said acoustic responses of the first and second pulses along with using the computed estimate (of position-and-orientation); and, displaying the image to a display.

In an embodiment, the step of computing said estimate of position-and-orientation comprises computing a Jacobian derivative with respect to changes of position-and-orientation. In an embodiment, computing a configuration estimate comprises computing a Jacobian derivative of a reconstructed image of the volume with respect to changes of configuration of the probe.

In an embodiment, the step of computing an image comprises minimization of error between measured responses (i.e. received acoustic responses) and predicted responses (e.g. acoustic responses computed using a computational model of a physical system). In an embodiment, the step of computing said estimate of position-and-orientation comprises minimization of error between measured responses and predicted responses.

In an embodiment, computed estimates of position-and-orientation are represented by affine transformations relative to a global coordinate reference 790.

In an embodiment, the step of computing an image comprises using a system matrix to generate predicted responses from the image. In an embodiment, the step of computing estimates of position-and-orientation comprises solving variables that represent a linearized approximation of motion for a predicted response. In an embodiment, the computed estimate of position-and-orientation comprises a relative motion estimate between the second configuration of the probe and the first configuration of the probe.

As described above, simultaneously solving a reconstructed image and a probe configuration (or a trajectory of multiple probe configurations) can be performed iteratively, whereby each outer iteration is a two step process, in accordance with equation (33).

In an embodiment, computing the configuration estimate comprises the steps of: computing a matrix of values (e.g. a Jacobian matrix) to account for effects of change of probe configuration (e.g. changes of position and orientation; changes along x, y or z axes; changes of roll, pitch or yaw) on acoustic responses; and, solving a variable representing change in probe configuration using the computed matrix by minimizing error between received acoustic responses (i.e. measured acoustic signals) and predicted acoustic responses. In an embodiment, computing the configuration estimate further comprises the step of: updating a previous configuration estimate with a solved variable representing change in configuration to produce an updated configuration estimate.

In an embodiment, the step of computing the configuration estimate further comprises applying a system response matrix to a computed Jacobian derivative to generate a matrix of values representing effects of change in probe configuration on acoustic responses.

Optimization Algorithms

It is well known in the art that an Accelerated Proximal Gradient (APG) algorithm solves a convex optimization problem of the form $$\underset{x}{\text{minimize}}\ f(x) + g(x) \qquad (37)$$

where g is a smooth convex function (e.g. the $\ell_2$ norm), and $f$ is a non-smooth convex function (e.g. the $\ell_1$ norm). In an embodiment, this can implement an image reconstruction problem similar to equation (9). The solution of (37) is iteratively obtained as $$x^{k+1} := \mathrm{prox}_{\rho f}(w^k - \rho \nabla g(w^k))$$

$$w^{k+1} := x^{k+1} + \beta_k(x^{k+1} - x^k) \tag{38}$$

where $\rho$ is a scaling parameter, $$\beta_k = \frac{k}{k+3},$$

and k is the iteration count. The initial values $x^0$ and $w^0$ are set to zero. Since g is smooth, its gradient $\nabla g$ can be computed analytically. For the non-smooth function, the proximal operator of $f$ is defined as $$\mathrm{prox}_{\tau f}(x) = \operatorname*{argmin}_{u}\left(f(u) + \frac{1}{2\tau}\|u - x\|_2^2\right) \tag{39}$$

where $\tau$ is a scaling constant. Many non-smooth functions have a proximal operator $\mathrm{prox}_f$ that is efficient to compute. However, when a function $f$ is composed with linear operator G, the resulting function $f \circ G$ does not necessarily have a similarly efficient proximal operator.

To deal with such a situation, it is well known in the art, that an Alternating Direction Method of Multipliers (ADMM) algorithm solves a convex optimization problem of the form $$\operatorname*{minimize}_{x,z}\ g(z) + \vartheta(x) \tag{40}$$

$$\text{subject to } z = Gx$$

Here, the variables x and z are both minimized. The solution to (40) is achieved by iteratively computing $$z^{k+1} := \operatorname*{argmin}_{z}\left(g(z) + \frac{\rho}{2}\|z - Gx^k - u^k\|_2^2\right) \tag{41}$$

$$x^{k+1} := \operatorname*{argmin}_{x}\left(\vartheta(x) + \frac{\rho}{2}\|Gx - z^{k+1} + u^k\|_2^2\right)$$

$$u^{k+1} := u^k + Gx^{k+1} - z^{k+1}$$

where u is a dual-update variable, and $\rho$ is a scaling parameter.

It is well known in the art that certain solver programs, including a Templates for First-Order Conic Solvers (TFOCS) algorithm, can handle a convex optimization problem in block composite form (BCF), represented as $$\operatorname*{minimize}_{v}\ \xi_0(v) + \sum_{i=1}^{m}\xi_i(L_i v - c_i) \tag{42}$$

where $$L = \begin{bmatrix} L_1 \\ \vdots \\ L_m \end{bmatrix},\ c = \begin{bmatrix} c_1 \\ \vdots \\ c_m \end{bmatrix}$$

Here, L is a block matrix containing m linear operator matrices $L_i$, and $c_i$ is an offset vector. The smooth function $\xi_0$ is applied to the composite vector v, and the functions $\xi_i$, i=1 ... m are applied to the domain $L_i v - c_i$. For convenience, in (42) the summation $$\sum_{i=1}^{m}\xi_i(L_i v - c_i)$$

can be written $\xi(Lv - c)$, where $\xi = [\xi_1, \ldots, \xi_m]$ is a function map. A TFOCS solver, rather than solving equation (42) directly, can minimize a dual optimization problem of the form $$\operatorname*{minimize}_{u}\ \xi_0^*\left(\sum_{i=1}^{m}L_i^T u_i\right) + \sum_{i=1}^{m}\xi_i^*(-u_i + c_i) \tag{43}$$

where $$\xi_0^*(v)$$

is the dual conjugate of $\xi_0(v)$ and $$\xi_i^*(u)$$

(u) is the dual conjugate of $\xi_i(v)$. This computation is more efficient because the linear operator matrices $L_i$ are moved from the non-smooth functions $\xi_i$ in (42) to the smooth function $$\xi_0^*$$

in (43). In this case, solving (43) with (38) requires the smooth-function gradient $$\nabla \xi_0^* = \mathrm{prox}_{\xi_0}$$

$=\mathrm{prox}_{\xi_0}$ and the dual-proximal operator $\mathrm{prox}_{\xi *}$, which can be obtained from $\mathrm{prox}_{\xi}$ using a mathematical identity. Accordingly, the solution of (43) is computed iteratively as $$v^{k+1} := \mathrm{prox}_{\tau\xi_0}(v^{k-\alpha_k} + \tau L^T w^k)$$

$$u^{k+1} := c - \mathrm{prox}_{\sigma\xi *}(c - w^k + \sigma L v^{k+1})$$

$$w^{k+1} := u^{k+1} + \beta_k(u^{k+1} - u^k) \tag{44}$$

where $$\beta_k = \frac{k}{k+3},\ \alpha_k = k - a\left\lfloor \frac{k}{a} \right\rfloor,$$

with $a \in \mathbb{Z}^+$, and $\sigma$ and $\tau$ are scaling parameters.

B) Real-Time Processing

In this section, a continuous real-time implementation of opto-acoustic reconstruction combined with solving a probe motion trajectory is described.

In an embodiment, real-time imaging involves displaying reconstructed images while a subject is being scanned. In an embodiment, during real-time scanning, images of a volume reconstructed at the probe's current position are continually output and displayed to a screen. In such a situation, it is apparent that new frames of data may continually arrive as input into a processing pipeline.

In general, the real-time display rate is limited by the processing time required for image reconstruction and other such processing stages. When the probe is manually positioned (e.g., by a human operator), its motion may also need to be determined, including position and orientation of the probe during each pulse's delivery and corresponding acquisition of resulting acoustic response signals.

To improve computational performance, in an embodiment, a pipeline caches outputs that are reused in subsequent computations. This reduces the number of iterations that an optimization-based solver (Appendix A) must perform.

An algorithm is developed (Algorithm 4) that resumes processing where it previously left off when a new frames arrives. To achieve this, at each repetition: i) a new coordinate reference frame is computed by "extrapolating forward" a probe's previously solved trajectory to a predicted position for the new acquisition; and, ii) the previously solved (cached) solutions are converted to the new reference frame by applying a homogeneous transform (according to the position predicted by extrapolation).

Real-Time Reconstruction and Motion Solving Using a Pipeline

In an embodiment, an opto-acoustic probe delivers optical energy pulses and acquires resulting acoustic response signals, which are then digitally processed.

In an embodiment, acoustic responses (acoustic signals) from the N most recent acquisitions are used to estimate probe positions and/or orientations (a.k.a. probe configurations). The responses, along with the estimated positions/ orientations, are used to reconstruct an image that is displayed in real-time. During continual system operation (see Algorithm 4 and FIG. 5), subsequent acquisitions are performed, which are used to reconstruct subsequent images that are displayed. At each repetition, to perform reconstruction, the N most recent acquisitions are used, which therefore may exclude some acquisitions used in earlier reconstructions.

To improve computational performance, reconstruction of the present repetition is seeded using an image generated by its preceding reconstruction. Specifically, a solver algorithm may use an earlier reconstruction as a starting solution (a.k.a, initial estimate) to speed up its processing and/or convergence. An image used as a starting solution may be spatially transformed (shifted) based on the probe velocity and/or motion trajectory, prior to its use. When no previous image has been solved, the starting solution may be set to all zeros.

Likewise, to improve computational performance for motion estimation, a subsequent estimate of probe positions/ orientations (i.e. rigid body configurations) may be seeded using a preceding estimate of probe positions/orientations. Specifically, a solver algorithm may use a preceding estimate of probe configuration as a starting solution. The starting solution for probe configurations may be transformed (spatially shifted) based on probe velocity and/or motion trajectory, prior to its use. In an embodiment, the starting solution is transformed to the probe's local coordinates according to an expected probe position computed based on extrapolating a probe trajectory.

In an embodiment, image reconstruction and a motion trajectory are solved using (sequential) convex optimization. An initial estimate of a reconstructed image and an initial estimate of probe positions and orientations, obtained during a previous repetition, may be used when processing reconstruction and motion information of a present repetition. In an embodiment, an accelerated proximal gradient algorithm is used to minimize error between measured acoustic responses and predicted responses. In an embodiment, the accelerated proximal gradient is initialized to the initial estimates(s). In an embodiment, measured acoustic responses (a.k.a. actual acoustic responses; received acoustic responses) are received by acoustic receivers.

In an embodiment, the processing stages of image reconstruction may be seeded with, initialized with or inputted with other data computed and stored during a preceding operation of the pipeline besides the preceding reconstructed image. Likewise, a subsequent estimate of probe positions/ orientations for motion estimation may be seeded with, initialized with or inputted with other data computed and stored during a preceding operation of the pipeline besides the preceding estimate of probe positions/orientations Probe Trajectories and Configuration Frames An illustration of probe trajectories 2101 and configuration frames 2103 is provided in FIG. 5 which shows two repetitions numbered as (i) and (i+1), in accordance with Algorithm 4. In an embodiment, this corresponds to a processing pipeline, where the value of i is incremented as new repetitions are continually processed. For each configuration frame 2103, rectangles with coordinate axes at their origins indicate the probe's position and orientation at acquisitions (i−N+1) to (i+1). Each repetition i computes a probe trajectory $p^{(i)}$, comprising N configuration frames, $$p_1^{(i)} \text{ to } p_N^{(i)},$$

which are shown surrounded by a dotted outline. The j-th frame of the trajectory $p^{(i)}$ is written $$p_j^{(i)}.$$

Figure 5:
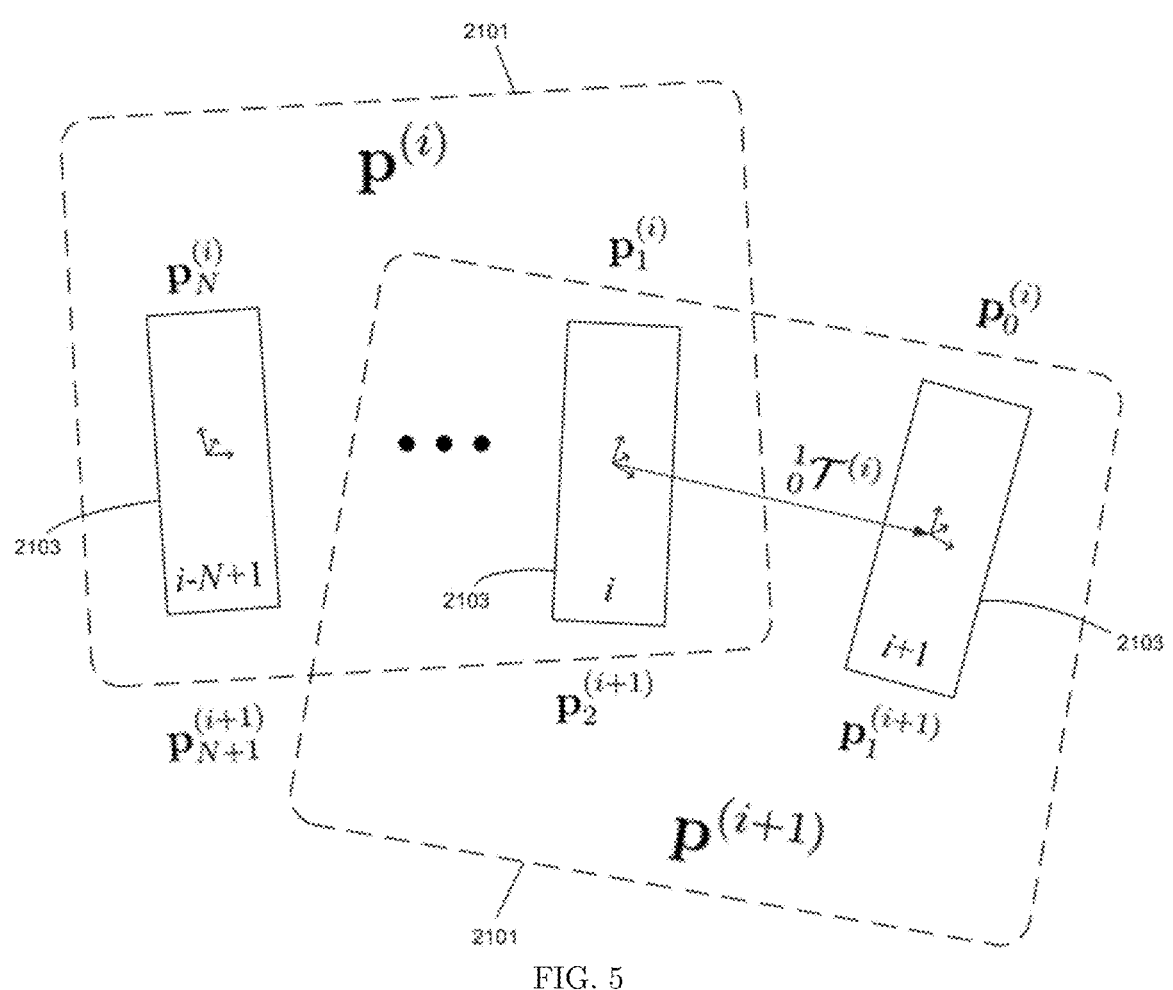
FIG. 5 is illustrative of probe trajectories and configuration frames, as used by Algorithm 4.

There are N−1 acquisitions that overlap between trajectories $p^{(i)}$ and $p^{(i+1)}$. FIG. 5 illustrates the case where N=2.

In the notation of this section, the most recent frame in a trajectory has index j=1. The next frame (of the future repetition) has index j=0, which is used as a reference frame in the trajectory about to be solved. Thus, in trajectory $p^{(i+1)}$, frame $$p_1^{(i+1)}$$

corresponds to the most recent acquisition of acoustic data, which was not available when the earlier trajectory $p^{(i)}$ was solved. In trajectory $p^{(i)}$, this same frame is represented by $$p_0^{(i)}.$$

The rigid body coordinate transform between $p^{(i)}$ and $p^{(i+1)}$ is written $$\prescript{1}{0}{\mathcal{T}}^{(i)},$$

as it corresponds to the difference between frames 1 and 0 in repetition i. This can be estimated by using probe motion from $p^{(i)}$.

In an embodiment, computing a trajectory $p^{(i)}$ with Algorithm 4 comprises running an iterative computation such as Algorithm 3, where a variable k represents a an iteration count. To distinguish repetition i from iteration k, a k-th iteration of $p^{(i)}$ can be written as $p^{(i)(k)}$. However, because Algorithm 4 is described separately from the other algorithms (Algorithm 1, Algorithm 2 and Algorithm 3), the distinction between $p^{(i)}$ and $p^{(k)}$ will be clear from the context, so writing $p^{(i)(k)}$ is not necessary. In other words, different algorithms may reuse local variable names.

Homogeneous Transformations

In Algorithm 4, to permit reuse of previous computations, it is desirable that the trajectory $p^{(i)}$ will be converted to new coordinates before $p^{(i+1)}$ is solved. A homogeneous transformation $$\prescript{l}{j}{\mathcal{T}} \in \mathbb{R}^{4 \times 4}$$

describes a rigid body configuration of coordinate frame j with respect to frame l. It is defined as $$\prescript{l}{j}{\mathcal{T}} = \begin{bmatrix} \prescript{l}{j}{\mathcal{R}} & \prescript{l}{j}{\mathcal{P}} \\ 0 & 1 \end{bmatrix}, \tag{45}$$

where $$\prescript{l}{j}{\mathcal{R}} \in \mathbb{R}^{3 \times 3}$$

is the rotation matrix to frame j with respect to l; and, the position vector $$\prescript{l}{j}{\mathcal{P}} \in \mathbb{R}^{3}$$

is the origin of j with respect to l.

The inverse of $$\prescript{l}{j}{\mathcal{T}}$$

is written $$\prescript{j}{l}{\mathcal{T}},$$

according to $$\left(\prescript{l}{j}{\mathcal{T}}\right)^{-1} = \prescript{j}{l}{\mathcal{T}} = \begin{bmatrix} \prescript{l}{j}{\mathcal{R}}^{T} & -\prescript{l}{j}{\mathcal{R}}^{T}\prescript{l}{j}{\mathcal{P}} \\ 0 & 1 \end{bmatrix}. \tag{46}$$

---

Algorithm 4 real-time opto-acoustic image reconstruction with motion tracking

Input: $y_i \in \mathbb{R}^{tm}$
Output: $x^{(i)}, \in \mathbb{R}^{n_v n_\mu}, p^{(i)} \in \mathbb{R}^{tp^{nf}}, i = 1, 2, \ldots$
1:   procedure CONTINUOUSOPERATION($y_1, y_2, \ldots$)
2:     $(y_0, \ldots, y_{1-N}) \leftarrow 0, (p_0, \ldots, p_{1-N}) \leftarrow 0, (x_0, \ldots, x_{1-N}) \leftarrow 0$   ▷ initialize to zero
3:     for i = 1 . . . do
4:       $\bar{y}^{(i+1)} \leftarrow \begin{bmatrix} y_{i-N+1} \\ \vdots \\ y_i \end{bmatrix}$   ▷ assemble acoustic measurements from N most recent frames
5:       compute current reference frame $p_0^{(i)}$
      by extrapolating forward the trajectory $p^{(i)}$
6:       extract $A_0^{(i)}$ and $b_0^{(i)}$
      from $p_0^{(i)}$
      using equation (19)
7:       $\prescript{1}{0}{\mathcal{T}}^{(i)} \leftarrow \begin{bmatrix} A_0^{(i)} & b_0^{(i)} \\ 0 & 1 \end{bmatrix}$   ▷ determine current homogeneous transform using equation (48)
8:       for j = 1 . . . N do
9:         extract $b_j^{(i)}$ and $A_j^{(i)}$
      from configuration $p_j^{(i)}$
      using equation (19)

US 12,651,391 B2

27                       28

-continued

| Algorithm 4 real-time opto-acoustic image reconstruction with motion tracking | |
|---|---|
| 10: $\quad \left[A_j^{(i+1)} \; b_j^{(i+1)}\right] \leftarrow \left({}_0^1\mathcal{T}^{(i)}\right)^{-1}\left[A_j^{(i)} \; b_j^{(i)}\right]$ | ▷ apply homogeneous transform (50) |
| 11: $\quad$ compute Euler angles $\theta_j^{(i+1)}$ | |
| $\qquad$ from rotation matrix $A_j^{(i+1)}$ | |
| 12: $\quad \tilde{p}_j^{(i+1)} \leftarrow \left(b_j^{(i+1)}, \theta_j^{(i+1)}\right)$ | ▷ update configuration estimate $\tilde{p}_j^{(i+1)}$ |
| | of frame j |
| 13: $\quad$ end for | |
| 14: $\quad \tilde{p}^{(i+1)} \leftarrow \begin{bmatrix} \tilde{p}_{(i-N+1)}^{(i+1)} \\ \vdots \\ \tilde{p}_i^{(i+1)} \end{bmatrix}$ | ▷ update initial state for $p^{(i+1)}$ |
| 15: $\quad \tilde{x}^{(i+1)} \leftarrow T_{p0}^{(i)} x^{(i)}$ | ▷ update initial state for $\tilde{x}^{(i+1)}$ by applying $T_{p0}^{(i)}$ |
| | defined in Section 50 |
| 16: $\quad \begin{bmatrix} x^{(i+1)} \\ p^{(i+1)} \end{bmatrix} \leftarrow \text{RECONSTRUCTIONANDTRACKING}\left(\tilde{y}^{(i+1)}, \begin{bmatrix} \tilde{x}^{(i+1)} \\ \tilde{p}^{(i+1)} \end{bmatrix}\right)$ | ▷ Alg. 3 with initial states |
| 17: $\quad$ output $x^{(i+1)}$ | |
| 18: $\quad$ end for | |
| 19: end procedure | |

Compound transformations, where $${}_j^l\mathcal{T}$$

is represented by $${}_j^k\mathcal{T}$$

followed by $${}_k^l\mathcal{T},$$

obey the rule $${}_j^l\mathcal{T} = {}_k^l\mathcal{T}\,{}_j^k\mathcal{T}. \qquad (47)$$

Estimation of Reference Frame

In an embodiment, the most recently acquired frame $$p_0^{(i)}$$

is used as a reference frame to solve repetition i+1. The position and orientation of $$p_0^{(i)},$$

which are described relative to $$p_1^{(i)},$$

are unknown during repetition i. Therefore, in repetition i+1, these are extrapolated from $p^{(i)}$.

FIG. 5 shows present trajectory $p^{(i+1)}$ with respect to known trajectory $p^{(i)}$. The homogeneous transformation $${}_0^1\mathcal{T}^{(i)}$$

represents predicted motion of the present acquisition. Using equation (45), this is equal to $${}_0^1\mathcal{T}^{(i)} = \begin{bmatrix} A_0^{(i)} & b_0^{(i)} \\ 0 & 1 \end{bmatrix} \qquad (48)$$

where $$A_0^{(i)} = {}_0^1\mathcal{R}^{(i)}$$

US 12,651,391 B2

29

30 is an estimated rotation matrix and $$b_0^{(i)} = {}_0^1 P^{(i)}$$

is an estimated displacement of frame 0 with respect to frame 1.

In an embodiment, the future position of a moving object can be predicted by analyzing its historical trajectory. Accordingly, motion estimation techniques that analyze a known trajectory, can be used to determine $$A_0^{(i)}$$

and $$b_0^{(i)}$$

by analyzing $p^{(i)}$. In particular, there are numerous approaches known in the art for prediction of a future trajectory based on a known trajectory, including those which involve attitude representations of inertial frames. Accordingly, in this manner the differential motion of the probe can be extrapolated forward to the new coordinate reference frame, as required by an algorithm described below.

Transformation to Current Frame

In repetition i+1, the position and orientation of each frame is described by $${}_j^1 T^{(i+1)},$$

which uses l=1 as the reference frame in equation (45). As illustrated by FIG. 5, coordinate frame 1 in iteration i+1 is the same as coordinate frame 0 in iteration i. Similarly, for each frame j, the transformation $${}_j^1 T^{(i+1)}$$

is equal to $${}_j^0 T^{(i)}.$$

Using equation (47), we obtain $${}_j^1 T^{(i+1)} = {}_j^0 T^{(i)}$$  (49a)

$$= {}_0^0 T^{(i)} {}_j^1 T^{(i)}.$$  (49b)

Here, the matrix $${}_1^0 T^{(i)}$$

can be determined by its inverse $${}_0^1 T^{(i)}$$

from equation (48) using equation (46). Thus, each frame of trajectory $p^{(i)}$ can be transformed to the present reference frame according to $$[A_j^{(i+1)} b_j^{(i+1)}] = ({}_0^1 T^{(i)})^{-1} [A_j^{(i)} b_j^{(i)}].$$  (50)

where $$A_j^{(i)} \in \mathbb{R}^{3\times3} \text{ and } b_j^{(i)} \in \mathbb{R}^3$$

are the rotation matrix and displacement of frame j from repetition i.

Algorithm for Continuous Operation

Algorithm 4 describes continuous real-time opto-acoustic image reconstruction and motion solving. The steps are as follows. First, on line 2, variables are initialized. Line 3 begins a main loop that runs for each repetition i, processing incoming frames of measured acoustic data $y_i$. On line 4, the N most recent frames of acoustic measurements are assembled into a data input vector $\tilde{y}^{(i+1)}$. On line 5, The current reference frame $$p_0^{(i)}$$

is computed by extrapolating forward the trajectory $p^{(i)}$, as described above. This is used to determine a current homogeneous transform $${}_0^1 T^{(i)}$$

on line 7. On lines 8 to 14, each previously solved frame is transformed relative to the reference frame, as described above. The estimated trajectory $\tilde{p}^{(i+1)}$ is specified using Euler angles with respect to the new reference frame. On line 15, the previously reconstructed volume $x^{(i)}$ is converted to a coordinate frame relative to the new reference frame by applying $$T_{p_0}^{(i)},$$

as defined above. Thus, the initial state for the reconstructed image is $$\tilde{x}^{(i+1)} = T_{p_0}^{(i)} x^{(i)}.$$

On line 16, the estimated trajectory and initial image state are passed to the optimization-based solver RECONSTRUCTION AND TRACKING of Algorithm 3. To improve processing time, the solver is initialized to the initial state $$\begin{bmatrix} \hat{x}^{(i+1)} \\ \hat{p}^{(i+1)} \end{bmatrix},$$

rather than being initialized to zero. If desired, other methods, such as fixed point iterations, smoothing, or adding constraints, can be used to "hint" the solution towards the initial estimate. Passing an initial state to the solver helps to maintain solutions near the true solution, resulting in faster convergence and computation. The call to Algorithm 3 returns an updated image and trajectory $$\begin{bmatrix} x^{(i+1)} \\ p^{(i+1)} \end{bmatrix}.$$

The resulting image $x^{(i+1)}$ can be output to a display to visualize a 2D or 3D region of tissue.

Method to Reconstruct and Display Opto-Acoustic Images in Real-Time with Solving Motion Trajectory The present invention includes a method to reconstruct and display opto-acoustic images in real-time with motion with solving a motion trajectory.

Figure 13:
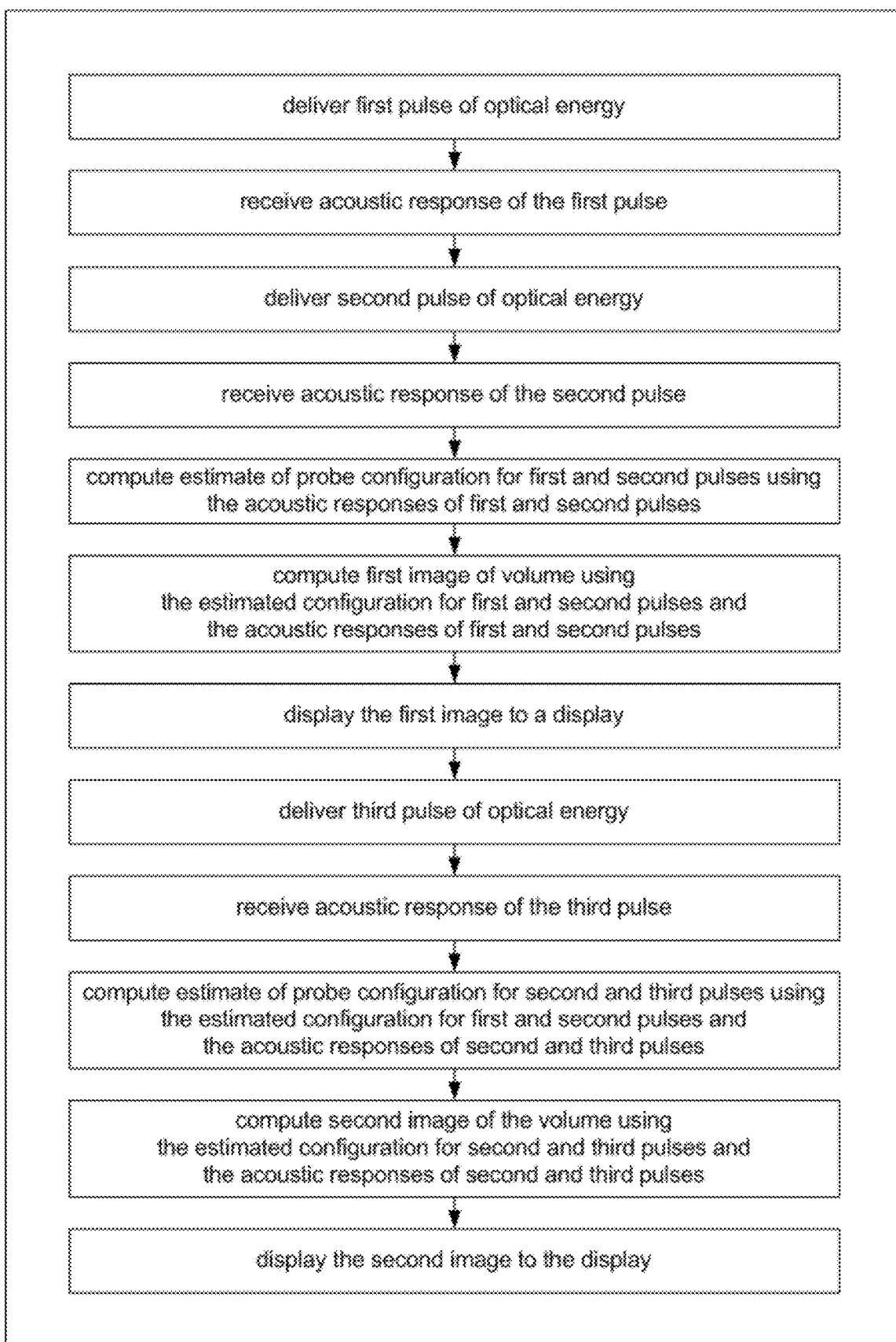
FIG. 13 is a flow diagram illustrating a process flow for real-time image reconstruction with solving of motion using a processing pipeline in accordance with an embodiment.

In an embodiment, the method is performed using an opto-acoustic probe that comprises: an optical exit port 720 adapted to deliver optical energy 730 to a volume; and, acoustic receivers to receive acoustic signals generated in response to absorbed optical energy. An opto-acoustic probe is illustrated in FIG. 6. FIG. 13 is a flow diagram illustrating a process flow for real-time image reconstruction with solving a motion trajectory using a processing pipeline.

In an embodiment, the probe continually delivers pulses of optical energy at a pulse repetition rate (e.g. 10 Hz); the acoustic receivers receive acoustic responses generated in response to each pulse; and, a processing subsystem processes each received acoustic response as input to a processing pipeline that generates images of the volume as output.

In an embodiment, the method comprises the steps of: delivering a first pulse of optical energy 731 to an optically absorbing volume 705 using an opto-acoustic probe 700 from a first position-and-orientation 791 (i.e. configuration) proximate to the volume; receiving a first set of acoustic responses 751 due to the first pulse; delivering a second pulse of optical energy 732 to the volume using the probe from a second first position-and-orientation 792 proximate to the volume; receiving a second set of acoustic responses 752 due to the second pulse; computing an estimate of probe positions for first and second pulses using: the received acoustic responses of the first pulse, and the received acoustic responses of the second pulse; computing a first image 781 of the volume using: the received acoustic responses of the first pulse, the received acoustic responses of the second pulse, and the estimate of probe positions for first and second pulses; displaying the first image to a display 780.

In an embodiment, the method further comprises: delivering a third pulse of optical energy 733 to the volume using the probe from a third position-and-orientation 793 proximate to the volume; receiving a third set of acoustic responses 753 due to the third pulse; computing an estimate of probe positions for second and third pulses using: the received acoustic responses of the second pulse, the received acoustic responses of the third pulse, and the estimate of probe positions for first and second pulses; computing a second image 782 of the volume using: the received acoustic responses of the second pulse, the received acoustic responses of the third pulse, and the estimate of probe positions for second and third pulses; and, displaying the second image to a display 780.

Figure 7:
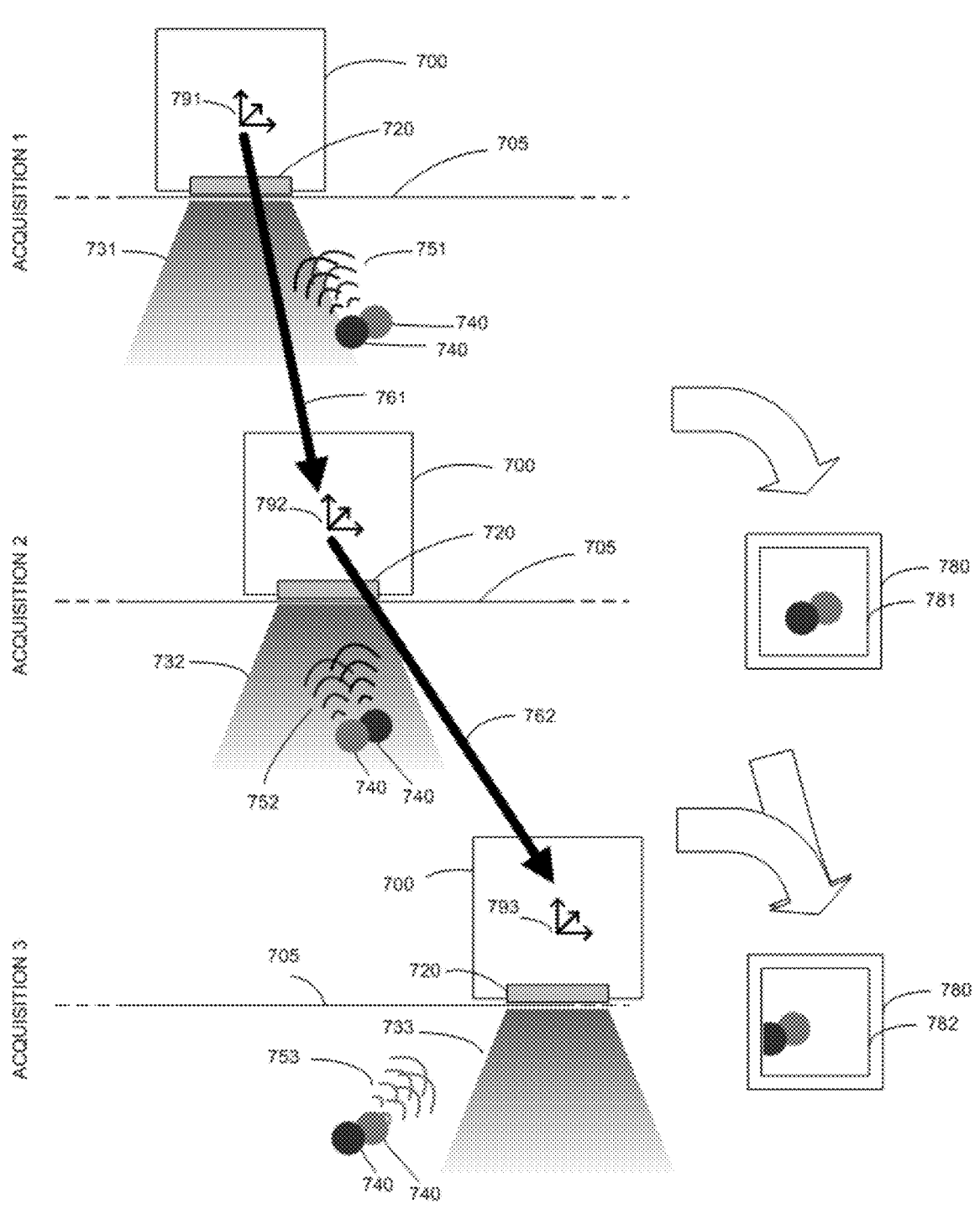
FIG. 7 is illustrative of relative changes of probe configurations during subsequent acquisitions and corresponding output to a display.

FIG. 7 illustrates an opto-acoustic probe during real-time acquisition.

In an embodiment, the step of computing said estimate of probe positions for first and second pulses comprises determining a probe configuration estimate for the second pulse relative to that of the first pulse 761. In an embodiment, the step of computing said estimate of probe positions for second and third pulses comprises determining a probe configuration estimate for the third pulse relative to that of the second pulse 762. In an embodiment, the step of computing said estimate of probe positions for second and third pulses comprises: computing a trajectory using estimated probe positions for first and second pulses; and, transforming the estimate of probe positions for first and second pulses according to the computed trajectory to produce transformed probe configurations.

In an embodiment, transforming an estimated probe configuration (i.e. probe position, probe orientation) comprises applying a homogeneous transformation, as described above, to extrapolate forward a previous estimate to a coordinate system for a subsequent estimate.

In an embodiment, the step of computing the second image 782 of the volume comprises: computing a trajectory using estimated probe positions for first and second pulses; and, transforming the first image of the volume according to the computed trajectory to produce a transformed image.

In an embodiment, transforming the first image comprises applying a rigid transformation to the first image.

In an embodiment, the step of computing a second image of the volume further comprises: inputting said transformed image to an optimization algorithm routine to facilitate minimization of an objective function. In an embodiment, the step of computing said estimate of probe positions for second and third pulses further comprises: inputting said transformed probe configurations to an optimization algorithm routine to facilitate minimization of an objective function.

In an embodiment, the step of computing said estimate of probe positions for second and third pulses further comprises: applying a rigid transformation to a probe configuration for the second pulse relative to that of the first pulse.

C) Uniform Motion Acquisition

Laser Triggering Controlled by Solved Motion of Probe

The present invention includes a method to perform laser triggering controlled by motion of probe to achieve desired physical spacing between frames.

In an embodiment, an opto-acoustic probe receives frames of acoustic data in response to emitted optical pulses. In certain circumstances, when a moving opto-acoustic probe is used, reconstructed image quality is higher if physical distances between acquisitions have a regular uniform spacing or a prescribed spacing.

However, when a human performs freehand scanning, a desired frame spacing does not generally occur because the frame acquisition rate is not synchronized with the probe's velocity. This can lead to artifacts in reconstructed images, including sidelobe and grating lobe artifact. To remedy this problem, the frame acquisition rate can be controlled dynamically by determining probe velocity and computing time intervals to occur between successive optical pulses.

Figure 14:
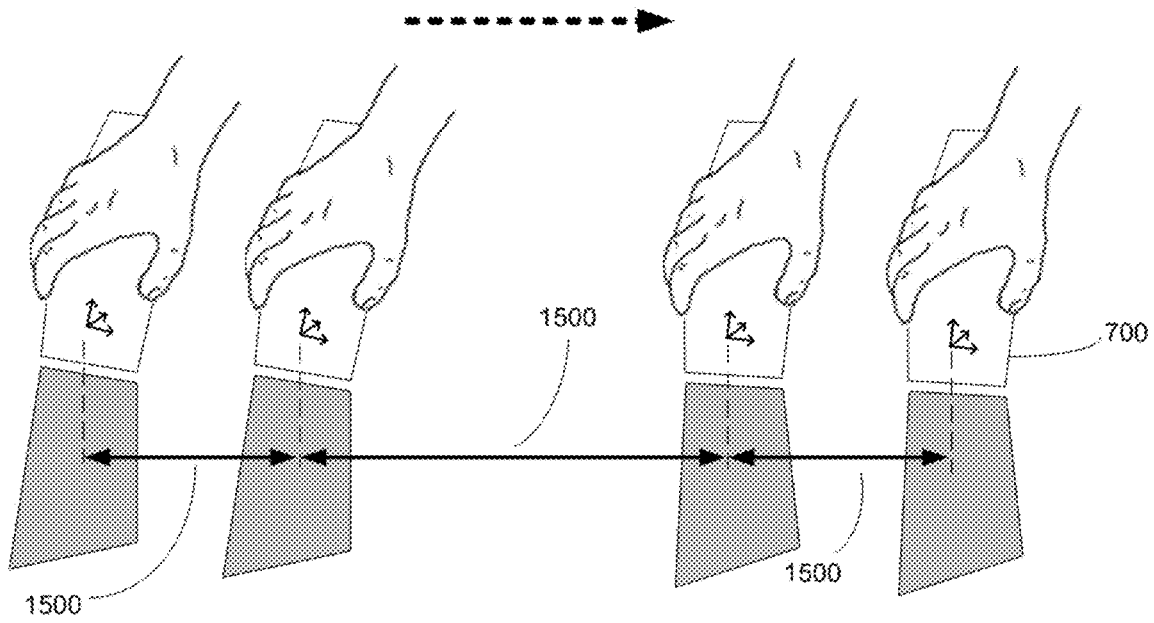
FIG. 14 is illustrative of a probe 700 in the process of acquiring frames with non-uniform interframe distances 1500.
Figure 15:
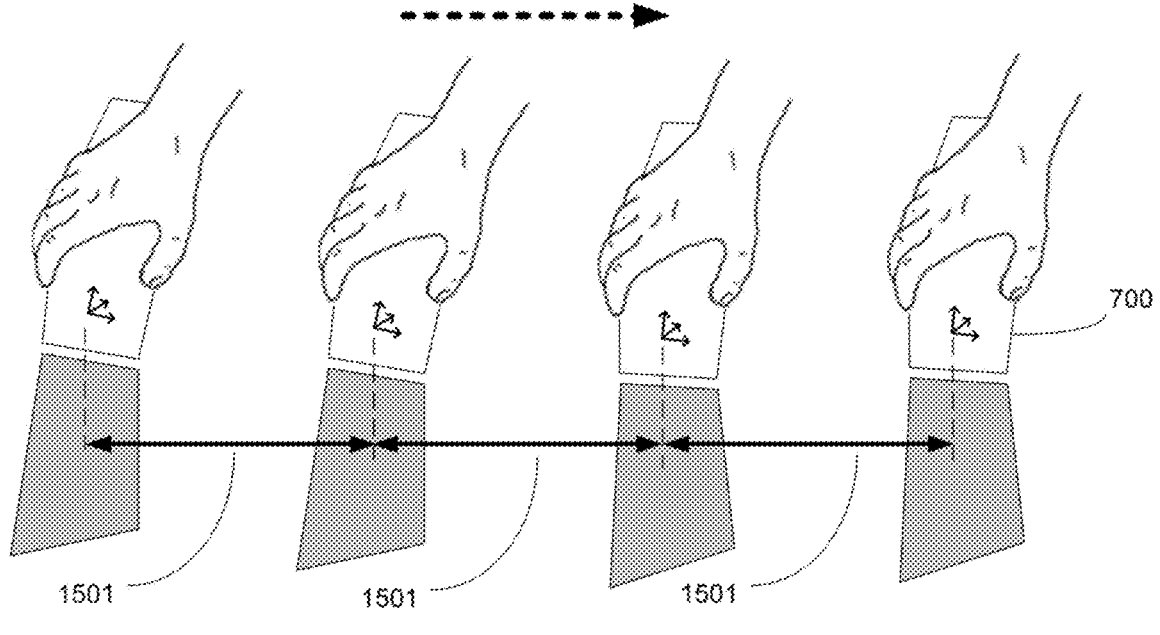
FIG. 15 is illustrative of a probe 700 in the process of acquiring frames with uniform interframe distances 1501.
Figure 16:
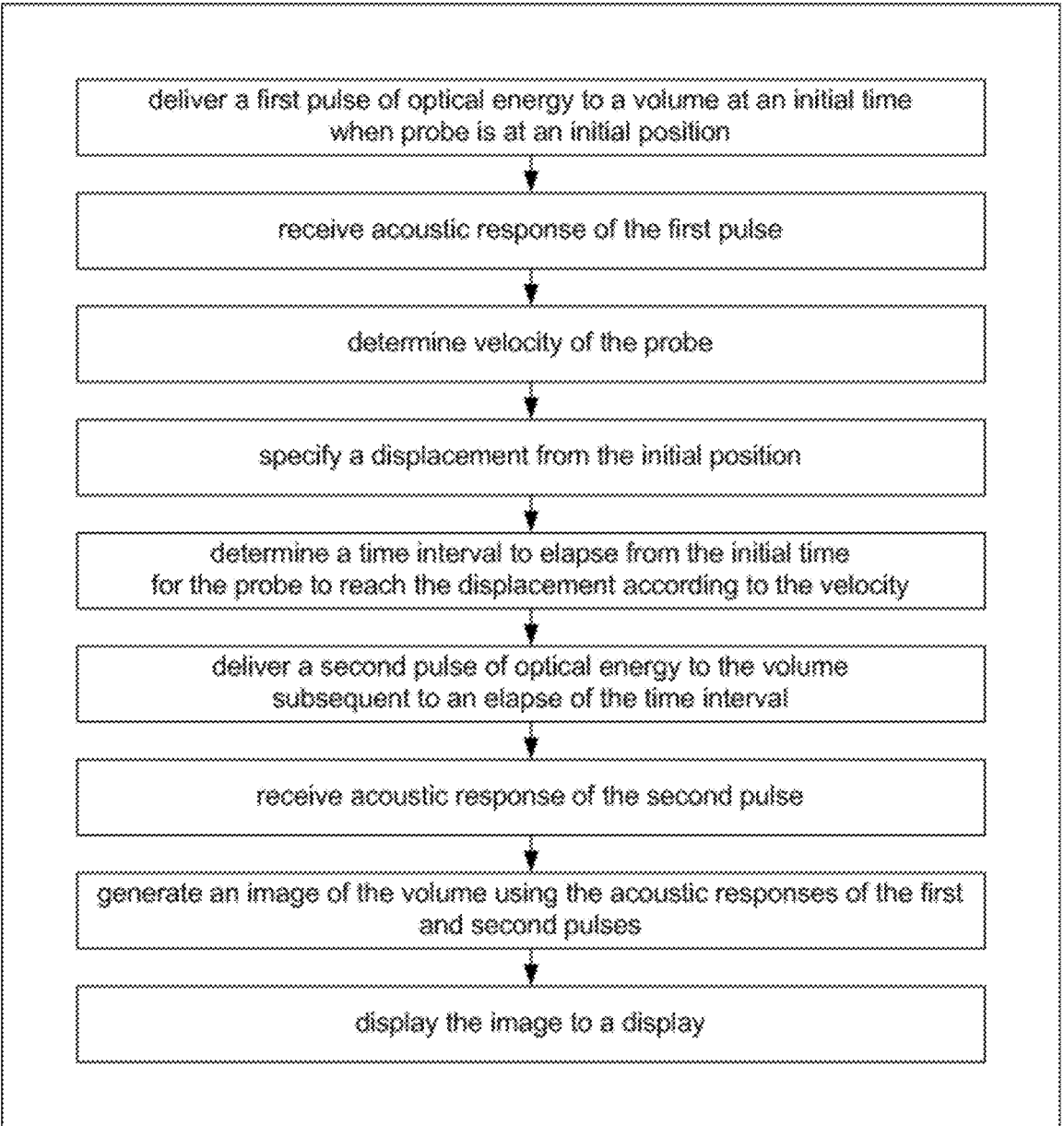
FIG. 16 is a flow diagram illustrating a process flow for uniform motion acquisition for image reconstruction with detecting motion in accordance with an embodiment.

FIG. 14 is illustrative of a probe 700 in the process of acquiring frames with non-uniform interframe distances 1500. FIG. 15 is illustrative of a probe 700 in the process of acquiring frames with uniform interframe distances 1501. FIG. 16 is a flow diagram illustrating a process flow for uniform motion acquisition for image reconstruction.

In an embodiment, determining probe velocity involves using opto-acoustic signals received by the probe. This may include performing motion tracking of the probe. Solving of the motion trajectory can estimate velocity along elevational axis (perpendicular to transducer elements of a linear array), or along lateral axis of the probe (parallel to transducer elements of a linear array). After a first optical pulse is delivered, a second optical pulse is delivered when a computed time interval elapses, corresponding to the probe reaching a specified displacement.

In the preferred embodiment, the computed time interval corresponds to the specified displacement divided by a determined velocity of the probe.

In an embodiment, an opto-acoustic probe comprises acoustic transducers to receive acoustic response signals; and, an optical exit port to deliver optical energy. In an embodiment, the probe receives acoustic response signals due to the optical pulses. In an embodiment, the acoustic response signals are used to reconstruct an image of a volume.

In an embodiment, a method comprises the steps of: providing an opto-acoustic probe; delivering a first pulse of optical energy to a volume at an initial time when the probe is positioned at an initial position; receiving acoustic responses of the first pulse; determining velocity of the probe; specifying a displacement from the initial position; determining a time interval after which the probe will reach the displacement according to its determined velocity; delivering a second pulse of optical energy to the volume following the time interval; receiving acoustic responses of the second pulse; generating an image of the volume using the acoustic responses of the first and second pulses; and, displaying the image to a display.

In an embodiment, the method further comprises determining the velocity of the probe using the acoustic responses of the first pulse. In an embodiment, the method further comprises determining the velocity of the probe using convex optimization for determining motion. In an embodiment, the displacement is along an elevational axis of the probe. In an embodiment, the displacement is along a lateral axis of the probe. In an embodiment, the probe is adapted to be held by a human who performs manual scanning.

The invention claimed is:

1. A method for opto-acoustic imaging with a probe, comprising the steps of:

delivering a first pulse of optical energy to an optically absorbing volume with the probe at a first probe configuration proximate to the volume;

receiving acoustic responses of the first pulse from the probe;

delivering a second pulse of optical energy to the volume with the probe at a second probe configuration proximate to the volume;

receiving acoustic responses of the second pulse from the probe;

computing a probe configuration estimate using the acoustic responses of the first and second pulses;

computing an image of the volume using the probe configuration estimate and the acoustic responses of the first and second pulses;

computing predicted acoustic responses using the image of the volume as input to a simulation, computing an updated probe configuration estimate by minimizing error between the predicted acoustic responses and the acoustic responses of the first and second pulses;

computing an updated image of the volume using the updated probe configuration estimate; and displaying the updated image to a display.

2. The method of claim 1, wherein the step of computing the probe configuration estimate comprises computing a Jacobian derivative of a reconstructed image of the volume with respect to changes of configuration of the probe.

3. The method of claim 2, wherein the step of computing the probe configuration estimate further comprises applying a system response matrix to the computed Jacobian derivative to generate a matrix of values representing effects of change in probe configuration on the acoustic responses of the first and second pulses.

4. The method of claim 1, wherein the step of computing the predicted acoustic responses comprises applying a system response matrix to the image.

5. The method of claim 1, wherein computing the updated probe configuration estimate further comprises:

updating a previous probe configuration estimate with a solved variable representing a change in probe configuration to produce the updated probe configuration estimate.

6. The method of claim 1, wherein the step of computing the image further comprises the steps of:

generating at least one intermediate slice of values by applying a separable factor of an acoustic response to a stored image representation; and, simulating at least a portion of the predicted acoustic responses by applying a separable co-factor of an acoustic response to the at least one intermediate slice of values.

7. The method of claim 1, wherein the first probe configuration comprises a first position and a first orientation of the probe, and the second probe configuration comprises a second position and a second orientation of the probe.

8. The method of claim 1, wherein the simulation comprises a system response matrix.

* * * * *